US012735685B2

(12) United States Patent
Wichelecki

(10) Patent No.: US 12,735,685 B2
(45) Date of Patent: Sep. 15, 2026

(54) ENZYMATIC PRODUCTION OF ALLULOSE

(71) Applicant: BONUMOSE, INC., Charlottesville, VA (US)

(72) Inventor: Daniel Joseph Wichelecki, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 691 days.

(21) Appl. No.: 17/925,168

(22) PCT Filed: May 18, 2021

(86) PCT No.: PCT/US2021/032952
§ 371 (c)(1),
(2) Date: Nov. 14, 2022

(87) PCT Pub. No.: WO2021/236632
PCT Pub. Date: Nov. 25, 2021

(65) Prior Publication Data

US 2023/0183768 A1 Jun. 15, 2023

Related U.S. Application Data

(60) Provisional application No. 63/026,294, filed on May 18, 2020.

(51) Int. Cl.

| | |
|---|---|
| ***C12N 9/12*** | (2006.01) |
| ***C12N 9/10*** | (2006.01) |
| ***C12N 9/58*** | (2006.01) |
| ***C12N 9/90*** | (2006.01) |

(Continued)

(52) U.S. Cl.
CPC ......... *C12N 9/1229* (2013.01); *C12N 9/1051* (2013.01); *C12N 9/90* (2013.01);
(Continued)

(58) Field of Classification Search
CPC ................................ C12N 9/90; C12N 9/1229
See application file for complete search history.

(56) References Cited

U.S. PATENT DOCUMENTS 10,704,069 B2 * 7/2020 Wichelecki .......... C12Y 501/03
11,053,528 B2 * 7/2021 Wichelecki ............ C12P 19/24
(Continued)

FOREIGN PATENT DOCUMENTS

| | | |
|---|---|---|
| TW | 201943854 A | 11/2019 |
| WO | 2018112139 A1 | 6/2018 |

(Continued)

OTHER PUBLICATIONS

A0A0E3NCH4_METTE. UniProtKB/TrEMBL Database. Apr. 10, 2019.*

(Continued)

*Primary Examiner* — Yong D Pak
(74) *Attorney, Agent, or Firm* — RAPHAEL BELLUM PLLC

(57) ABSTRACT

The invention relates to improved processes for the enzymatic production of allulose using enzymes which have been characterized as having improved expression, improved stability, and low allulose to fructose conversion activity, relative to enzymes in other allulose production methods. Improved processes include steps of converting fructose-6-phosphate to allulose 6-phopsphate A6P) using an allulose 6-phosphate epimerase, and converting A6P to allulose using an allulose-6-phosphate phosphatase.

19 Claims, 6 Drawing Sheets

Specification includes a Sequence Listing.

(51) Int. Cl.
*C12N 9/92* (2006.01)
*C12P 19/24* (2006.01)

(52) U.S. Cl.
CPC ................ *C12N 9/92* (2013.01); *C12P 19/24* (2013.01); *C12Y 204/01001* (2013.01); *C12Y 204/01018* (2013.01); *C12Y 501/03* (2013.01); *C12Y 503/01009* (2013.01); *C12Y 504/02002* (2013.01)

(56) References Cited

U.S. PATENT DOCUMENTS 11,078,506 B2 * 8/2021 Wichelecki .......... C12N 9/1051
11,168,342 B2 * 11/2021 Wichelecki ............. C12N 9/16

FOREIGN PATENT DOCUMENTS

WO 2018129275 A1 7/2018
WO 2018169957 A1 9/2018
WO 2020235830 A1 11/2020
WO 2021011881 A1 1/2021

OTHER PUBLICATIONS

Fransceus. J Ind Microbiol Biotechnol. May 2017;44(4-5):687-695.*

Sanavia. Computational and Structural Biotechnology Journal, vol. 18, 2020, pp. 1968-1979.*

Studer (Residue mutations and their impact on protein structure and function: detecting beneficial and pathogenic changes. Biochem. J. (2013) 449, 581-594.*

A0A223HZI7. UniProtKB/TrEMBL. Dec. 20, 2017.*

International Search Report and Written Opinion in International Application No. PCT/US2021/032952, dated Nov. 17, 2021.

UniProtKB submission A0A223HZI7, Allulose-6-phosphate 3-epimerase, Oct. 25, 2017.

* cited by examiner

FIG. 5

ENZYMATIC PRODUCTION OF ALLULOSE

CROSS-REFERENCE TO RELATED APPLICATIONS

This application claims priority to U.S. Application Ser. No. 63/026,294, filed on May 18, 2020, which is incorporated herein by reference in its entirety.

SEQUENCE LISTING

The Sequence Listing submitted herewith is an ASCII text file (2021-05-18_Sequence_Listing_ST25, created on May 18, 2021, 48,103 bytes) via EFS-Web is hereby incorporated by reference.

FIELD OF THE INVENTION

The invention relates to improved enzymatic processes for producing D-allulose.

BACKGROUND

D-allulose, which is also known as D-psicose, or simply, allulose, is a low-calorie, natural sweetener with 70% the sweetness of sucrose, but only 10% of its calories. It is a naturally occurring monosaccharide hexose, and is present in small amounts in wheat and other plants. Allulose was approved as a food additive by the Food and Drug Administration (FDA) in 2012, which designated it as generally recognized as safe (GRAS). However, allulose's high cost has limited its use as a sweetener. Nevertheless, in addition to having 10% of the calories of sucrose, Allulose boasts numerous health benefits, including a low glycemic index of 1; full absorbtion in the small intestine without being metabolized, resulting in its elimination in urine and feces; and inhibition of alpha-amylase, sucrase and maltase to help regulate blood sugar—all while having a functionality in foods and beverages that is similar to that of sucrose. As such, allulose has a variety of applications in the food and beverage industries.

Allulose is produced, predominantly, by methods involving enzymatic isomerization of fructose. See, for example, PCT Application Publication No. WO 2014/049373. Overall, such methods are not commercially viable because the costly separation of allulose from fructose, and relatively low product yields associated with them result in higher feedstock costs.

An alternative process for producing allulose by using an epimerase to catalyze fructose 6-phosphate to allulose 6-phosphate, followed by a dephosphorylation step is described in PCT Application Publication Nos. WO 2018/112139, WO 2018/004308, and WO 2018/129275, but these, and other alternative allulose production methods, do not satisfy a long-standing need for a process for producing allulose that provides a higher yield, using lower amounts of enzymes. With such improvements in mind, the following disclosure describes enzymes for use in the production of allulose, which have greater expression, stability, and are associated with low undesired allulose conversion activity, relative to currently employed allulose production methods. The foregoing improvements meet a strong industrial and commercial interest in decreasing the cost of allulose production.

SUMMARY OF THE INVENTION

The invention provides improved allulose preparation methods of enzymatically converting saccharides, such as, for example, polysaccharides, oligosaccharides, disaccharides, sucrose, D-glucose, and D-fructose into allulose. In one aspect, an improved process of the invention for the production of allulose from a saccharide includes a step of converting fructose-6-phosphate (F6P) to allulose 6-phopsphate (A6P), using an allulose 6-phosphate epimerase (A6PE), wherein the A6PE comprises an amino acid sequence having at least 90% sequence identity to SEQ ID NO: 1. In another aspect, an improved process according to the invention for the production of allulose from a saccharide includes a step of converting A6P to allulose, using an allulose-6-phosphate phosphatase (A6PP), wherein the A6PP comprises an amino acid sequence having at least 90% sequence identity to SEQ ID NO: 2. In an embodiment of the invention, the improved process includes a step of converting fructose-6-phosphate (F6P) to allulose 6-phopsphate (A6P), using an allulose 6-phosphate epimerase (A6PE), wherein the A6PE comprises an amino acid sequence having at least 90% sequence identity to SEQ ID NO: 1, and a step of converting A6P to allulose using a allulose-6-phosphate phosphatase (A6PP), wherein the A6PP comprises an amino acid sequence having at least 90% sequence identity to SEQ ID NO: 2.

A process of the invention for preparing allulose may also involve converting glucose 6-phosphate (G6P) to F6P, in a step catalyzed by phosphoglucoisomerase (PGI). Other processes according to the invention may further include a step of converting glucose 1-phosphate (G1P) to G6P by a reaction catalyzed by phosphoglucomutase (PGM), while still other processes may further include conversion of a saccharide to G1P by a reaction catalyzed by at least one other enzyme.

Saccharides used in any of the processes described herein can be selected from a group consisting of a starch or its derivative, cellulose or its derivative, and sucrose. In that regard, a starch or its derivative can be, for example, amylose, amylopectin, soluble starch, amylodextrin, maltodextrin, maltose, maltotriose, or glucose. In some improved processes of the invention, starch is converted to a starch derivative by enzymatic hydrolysis or by acid hydrolysis of starch. Examples of enzymatic hydrolysis of starch to yield a starch derivative include, but are not limited to, reactions catalyzed by isoamylase, pullulanase, alpha-amylase, or a combination of two or more of these enzymes. Some processes of the invention can additionally involve adding 4-glucan transferase (4GT).

Other processes of the invention for preparing allulose further include a step of converting fructose to F6P, catalyzed by at least one enzyme. Other processes of the invention further include a step of converting sucrose to the fructose, in a reaction catalyzed by at least one enzyme. G6P, which is used in processes for preparing allulose can also be generated by converting glucose to the G6P, in a reaction catalyzed by at least one enzyme. Glucose can, in turn, be produced by converting sucrose to glucose, catalyzed by at least one enzyme.

Processes of the invention can be conducted under various reaction conditions, including at a temperature ranging from about 37° C. to about 85° C., at a pH ranging from about 4 to about 9, and/or for about 0.5 hour to about 48 hours, or as continuous reactions. In some embodiments, the steps of a process for preparing allulose are conducted under any one or more of the foregoing reaction conditions in a single reactor. While, in other embodiments, reaction steps are conducted under the foregoing reaction conditions using a plurality of bioreactors, which may be arranged in a series.

In some processes of the invention, the steps for preparing allulose are conducted under conditions that do not contain adenosine triphosphate (ATP) or NAD(H), i.e., ATP-free or NAD(H)-free, at a phosphate concentration from about 0.1 mM to about 150 mM, the phosphate is recycled, and/or the step of converting A6P to allulose involves an energetically favorable chemical reaction.

BRIEF DESCRIPTION OF THE FIGURES

FIG. 5 shows an enzymatic pathway converting sucrose or its derived products to allulose. SP, sucrose phosphorylase; PPFK, polyphosphate fructokinase; PGM, phosphoglucomutase; PGI, phosphoglucoisomerase; A6PE, allulose 6-phosphate epimerase; A6PP, allulose 6-phosphate phosphatase. In processes of the invention, the A6PE comprises an amino acid sequence having at least 90% sequence identity to SEQ ID NO: 1, and/or the A6PP comprises an amino acid sequence having at least 90% sequence identity to SEQ ID NO: 2.

DETAILED DESCRIPTION

Figure 1:
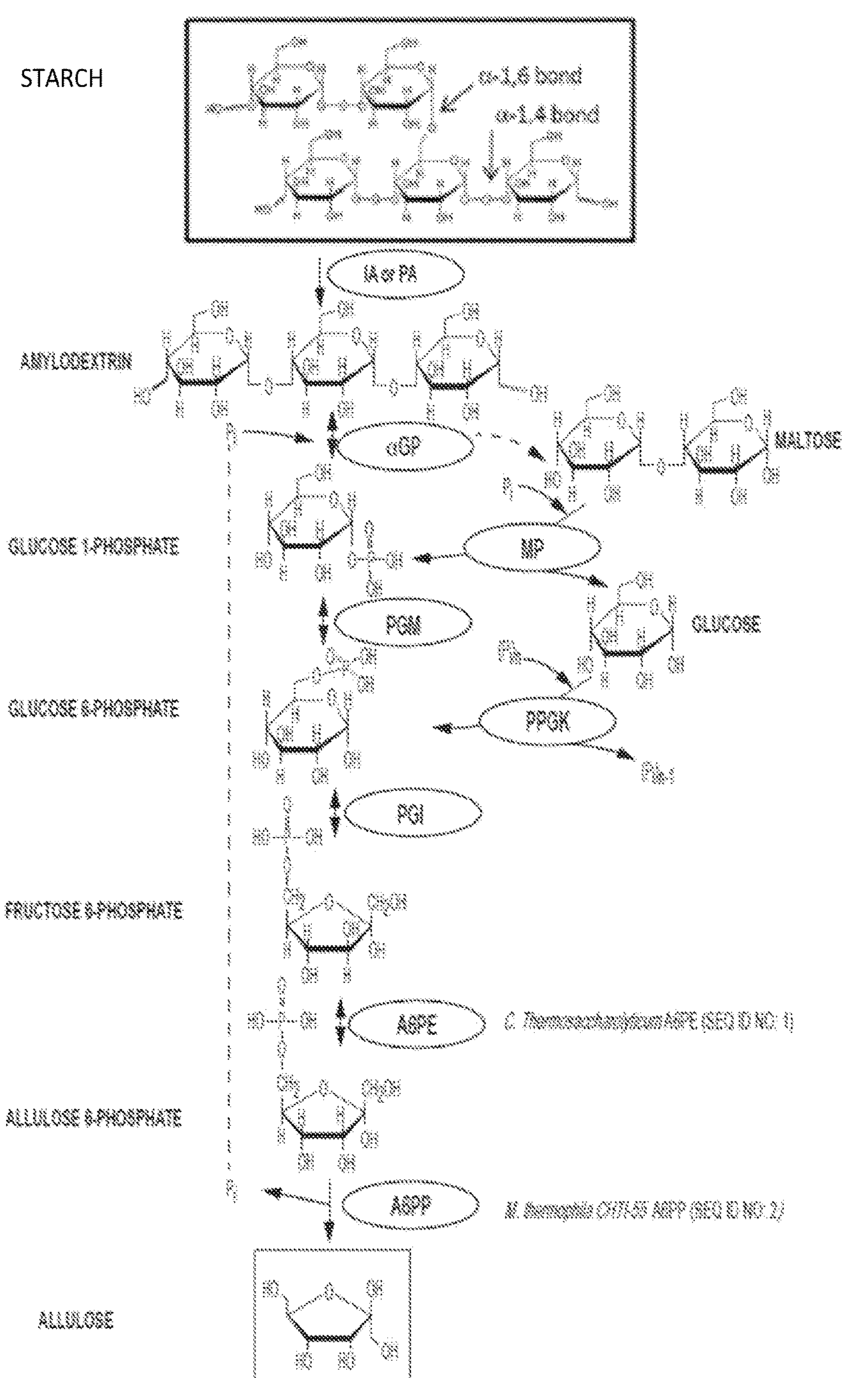
FIG. 1 is a schematic diagram illustrating an enzymatic pathway converting starch or its derived products to allulose. The following abbreviations are used: αGP, alpha-glucan phosphorylase or starch phosphorylase; PGM, phosphoglucomutase; PGI, phosphoglucoisomerase; A6PE, allulose 6-phosphate epimerase; A6PP, allulose 6-phosphate phosphatase; IA, isoamylase; PA, pullulanase; MP, maltose phosphorylase; PPGK, polyphosphate glucokinase. In processes of the invention, the A6PE comprises an amino acid sequence having at least 90% sequence identity to SEQ ID NO: 1, and/or the A6PP comprises an amino acid sequence having at least 90% sequence identity to SEQ ID NO: 2.

The invention described here relates to improved enzymatic processes for converting saccharides to allulose. More particularly, the invention relates to improved cell-free, enzymatic processes for the conversion of saccharides to allulose. Examples of saccharides, which may be converted to allulose by a process of the invention include, but are not limited to, starch, cellulose, sucrose, glucose, fructose, and products derived from any the foregoing saccharides. Enzymes used in a process according to the invention may be combined into a single cell-free enzyme cocktail. Indeed, in comparison to cell-based manufacturing methods for producing allulose, a process according provides higher reaction rates due, at least in part, to the absence of cell membranes, which can slow down the transport of substrate, product, or both, into and out of the cells used in the process. Processes of the invention also yield a final allulose product that is free of nutrient-rich metabolites associated with fermentation media and cells used in cell-based processes.

Some processes of the invention for producing allulose improve the step of converting fructose-6-phosphate (F6P) to allulose 6-phosphate (A6P) by a reaction catalyzed by an allulose 6-phosphate epimerase (A6PE), which has one or more improved properties relative to any one of the A6PE enzymes used in allulose production methods prior to the invention. Other processes of the invention improve the step of converting A6P to allulose by a reaction catalyzed by an allulose-6-phosphate phosphatase (A6PP), which has one or more improved properties relative to any one of the A6PP enzymes used in allulose production methods prior to the invention. In some processes of the invention, the process for producing allulose may include (F6P to A6P) and (A6P to allulose) conversion steps in which an improved A6PE and an improved A6PP are used for the (F6P to A6P) and (A6P to allulose) conversion steps, respectively. Other processes of the invention for producing allulose may use an improved A6PE for the F6P to A6P conversion step, while using an unimproved A6PP for the A6P to allulose conversion step. Conversely, there are also processes of the invention that use an unimproved A6PE for the F6P to A6P conversion step, and an improved A6PP for the A6P to allulose conversion step. See PCT Publication WO2018/112139, which is herein incorporated by reference in its entirely, for examples of A6PEs and A6PPs, including A6PE from *Thermoanaerobacterium thermosaccharolyticum* (UniProt ID D9TQJ4), A6PE from *Bacillus thermoamylovorans* (UniProt ID A0A090IXZ8), and A6PP from *Clostridium thermocellum* (UniProt ID A3DC21).

Using enzymes with higher activities and more favorable properties, such as improved stability, in a process for producing allulose allows for using lower amounts of enzymes, thereby reducing the cost of the overall process. As discussed above, the conversion of F6P to A6P in an improved process of the invention is catalyzed by an A6PE with improved properties, which contribute to improvements in an allulose production process, including one or more of the following improved properties: a higher expression yield, thermostability, and low undesired allulose to fructose epimerization activity, which is also referred to as fructose reversion, in comparison to the thermophilic A6PE from *Thermoanaerobacterium thermosaccharolyticum* (UniProt ID D9TQJ4).

In some processes of the invention, the expression yield of an A6PE in an improved process has an expression yield, which is at least 10%, at least 20%, at least 30%, at least 40%, at least 50%, at least 60%, at least 70%, at least 80%, at least 90%, at least 100%, at least 200%, at least 300% or at least 400% higher than the expression yield of an A6PE in an unimproved process such as, but not limited to, an A6PE with an amino acid sequence of UniProt ID D9TQJ4 (*Thermoanaerobacterium thermosaccharolyticum*). For example, in a process the invention for producing allulose, the step of converting F6P to A6P uses an A6PE with an amino acid sequence of UniProt ID A0A223HZI7 (*Clostridium thermosaccharolyticum*) with an expression yield, which is approximately 300%, 310%, 320%, 330%, 340%, 350%, 360%, 370%, 380%, 390%, or 400% higher than an A6PE with an amino acid sequence of UniProt ID D9TQJ4.

In some processes of the invention, an A6PE in an improved process is more stable than an A6PE in an unimproved process. More particularly, an A6PE in an improved process of the invention may be more thermostable than A6PE in an unimproved process. Indeed, the A6PE in some processes of the invention may remain 50%-60% soluble, 60%-70% soluble, 70%-80% soluble, 80%-90% soluble, 90%-100% soluble, or 100% soluble, after 30 minutes at 50° C.-60° C. In a process of the invention in which the conversion of F6P to A6P uses an A6PE in an improved process with an amino acid sequence of UniProt ID A0A223HZI7, the A6PE may remain about 80% soluble after 30 minutes at about 60° C.; therefore, the A6PE in an improved process may be at least 75%, 76%, 77%, 78%, 79%, 80%, 81%, 82%, 83%, 84%, or 85% soluble after 25, 26, 27, 28, 29, 30, 31, 32, 33, 34, or 35 minutes at 54° C., 55° C., 56° C., 57° C., 58° C., 59° C., 60° C., 61° C., 62° C., 63° C., 64° C., 65° C., or 66° C.

The conversion of allulose to fructose by A6PE in a process for producing allulose is undesirable. In some improved processes of the invention, A6PE-dependent allulose to fructose conversion activity is lower than it is in unimproved processes for producing allulose. In an improved process of the invention, for example, no more than 1%, no more than 0.9%, no more than 0.8%, no more than 0.7%, no more than 0.6%, no more than 0.5%, no more than 0.4%, no more than 0.3%, no more than 0.2%, no more than 0.1%, or 0% of allulose produced by a process of the invention is converted to fructose.

A6PE enzymes used in improved processes of the invention are specific for F6P/A6P, and the epimerization catalyzed by the A6PE is reversible. The term "specific", as used here, means the F6/A6P epimerization activity of an A6PE in an improved process of the invention is higher than it is for other phosphorylated monosaccharides present in the reaction. For example, the F6P/A6P epimerization activity of the A6PE in an improved process of the invention is higher than its epimerization activity for G6P.

The F6P to A6P conversion in improved processes of the invention may utilize a divalent metal A6PE cofactor, such as magnesium, manganese, cobalt, or zinc. In some processes of the invention, for example, cobalt is a cofactor of A6PE in the F6P to A6P conversion reaction step.

As discussed above, examples of properties of A6PE enzymes in improved processes of the invention include, but are not limited to, increased expression yield, increased stability, and decreased conversion of allulose to fructose. In some improved processes of the invention, the amino acid sequence of the A6PE thermophilic. More particularly, the A6PE in certain improved processes of the invention has an amino acid sequence, which shares 85%, 86%, 87%, 88%, 89%, 90%, 91%, 92%, 93%, 94%, 95%, 99%, or 100% sequence identity with an A6PE from *Clostridium thermosaccharolyticum*. Accordingly, in some improved processes of the invention, the amino acid sequence of the A6PE shares 85%, 86%, 87%, 88%, 89%, 90%, 91%, 92%, 93%, 94%, 95%, 99%, or 100% sequence identity with the amino acid sequence of the *C. thermosaccharolyticum* thermophilic epimerase with the sequence of UniPRot ID A0A223HZI7.

Another structural feature of A6PE in some improved processes of the invention is an $(\alpha/\beta)8$-barrel domain for catalysis. In some of those improved processes of the invention, the $(\alpha/\beta)8$-barrel domain contains a phosphate binding domain with a Ser at the end of the $7^{th}$ β strand of the barrel, a Ser at the end of the $8^{th}$ β-strand of the barrel, and a Gly in the active site loop. In other improved processes of the invention, the A6PE contains a metal binding domain with a His in the $2^{nd}$ and $3^{rd}$ β-strands of the barrel. In other improved processes of the invention, the A6PE contains an Asp in the $2^{nd}$ and $7^{th}$ β-strand of the barrel to act as the acid/base catalyst for 1,1 proton transfer. In other improved processes of the invention, the A6PE contains a His hydrophobic residue-Asp signature in the $2^{nd}$ β-strand of the barrel where the His is utilized in metal binding and the Asp for acid/base catalysis. In other improved processes of the invention, the A6PE is a member of the Ribulose-phosphate 3 epimerase family (Pfam PF00834). In yet other improved processes of the invention, the A6PE contains two or more of any of the $(\alpha/\beta)8$-barrel domain structural features described above. Accordingly, in some improved processes of the invention, the A6PE contains an $(\alpha/\beta)8$-barrel domain for catalysis, a Ser at the end of the 7th β-strand of the barrel, a Ser at the end of the $8^{th}$ β strand of the barrel, a Gly in the active site loop, a His in the $2^{nd}$ and $3^{rd}$ β-strands of the barrel, an Asp in the 2nd and 7th β-strand of the barrel, a His-hydrophobic residue-Asp signature in the 2nd β-strand of the barrel, and is a member of the Ribulose-phosphate 3 epimerase family (Pfam PF00834) These features of $(\alpha/\beta)$ 8-barrel domains are known in the art, and are referenced in, for example, Chan et al. Structural Basis for Substrate Specificity in Phosphate Binding (beta/alpha)8-Barrels: D-Allulose 6-Phosphate 3-Epimerase from *Escherichia coli* K-12. *Biochemistry* 2008; 47(36):9608-9617.

In an improved processes of the invention, allulose-6-phosphate phosphatase (A6PP) is a phosphatase that specifically converts A6P to allulose. Thus, an A6PP in an improved processes of the invention is specific for A6P. The term "specific", as used here, means the A6P dephosphorylation activity of A6PP is higher than it is for other phosphorylated monosaccharides in the process. For example, an A6PP of the improved process of the invention has a higher dephosphorylation activity on A6P than on G1P, G6P, and F6P. The A6PP in an improved process of the invention may also utilize a divalent metal cofactor, such as zinc, manganese, cobalt, or magnesium, preferably magnesium.

The conversion of A6P to allulose in an improved process of the invention may use an A6PP with increased activity relative to any of the A6PP enzymes used in processes for producing allulose prior to the invention. In some improved processes of the invention, for example, A6PP converts A6P to allulose with a higher activity than A6PP from *Clostridium thermocellum* (UniProt ID A3DC21). See International Patent Application Publications WO 2018/112139 and WO 2018/129275, which are herein incorporated by reference in their entireties. More particularly, in an improved process of the invention, the A6PP has an amino acid sequence of an A6PP from *Methanosarcina thermophila* CHTI-55, with A6P to allulose activity, which is improved by at least 10%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to the activity of the A6PP from *Clostridium thermocellum* with an amino acid sequence of UNIPROT ID A3DC21. Even more particularly, in some improved processes of the invention, the A6PP has an amino acid sequence of Uniprot ID A0A0E3NCH4 (SEQ ID NO. 2) with A6P to allulose activity, which is improved by at least 10%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to the activity of the A6PP from *Clostridium thermocellum* with an amino acid sequence of UNIPROT ID A3DC21.

In some improved processes of the invention, the A6PP has an amino acid sequence, which shares 85%, 86%, 87%, 88%, 89%, 90%, 91%, 92%, 93%, 94%, 95%, 99%, or 100% sequence identity with an A6PP from *Methanosarcina thermophila* CHTI-55. Accordingly, in some improved processes of the invention, the amino acid sequence of the A6PP shares 85%, 86%, 87%, 88%, 89%, 90%, 91%, 92%, 93%, 94%, 95%, 99%, or 100% sequence identity with the amino acid sequence of the *Methanosarcina thermophila* CHTI-55 phosphatase with the sequence of UniProt ID A0A0E3NCH4 (SEQ ID NO. 2).

Another structural feature of A6PE in some improved processes of the invention is a Rossmanoid fold domain for catalysis. In some of those improved processes of the invention, the A6PP contains one or more of the following features: a C1 capping domain for substrate specificity; a D×D signature in the 1st β-strand of the Rossmanoid fold for coordinating magnesium, where the second Asp is a general acid/base catalyst; a Thr or Ser at the end of the 2nd β-strand of the Rossmanoid fold that helps stability of reaction intermediates; a Lys at the N-terminus of the α-helix C-terminal to the 3rd β-strand of the Rossmanoid fold that helps stability of reaction intermediates; and a E(D/N) signature at the end of the 4th β-strand of the Rossmanoid fold for coordinating divalent metal cations, such as magnesium. See e.g., Burroughs et al., Evolutionary Genomics of the HAD Superfamily: Understanding the Structural Adaptations and Catalytic Diversity in a Superfamily of Phosphoesterases and Allied Enzymes. J. Mol. Biol. 2006; 361; 1003-1034. As established herein, an improved process of the invention includes a step of converting F6P to A6P, using an A6PE, and a step of converting A6P to allulose, using an A6PP. An improved process of the invention may also include additional upstream steps. For example, some processes of the invention produce allulose from a saccharide using phosphoglucose isomerase (PGI) to convert glucose 6-phosphate (G6P) to F6P. Exemplary PGIs which may be used include those disclosed in International Patent Application Publication WO2017/059278: PGI from *Clostridium thermocellum* (Uniprot ID A3DBX9) and PGI from *Thermus thermophilus* (Uniprot ID Q5SLL6).

Some improved processes of the invention also include a step of converting glucose 1-phosphate (G1P) to G6P using phosphoglucomutase (PGM). An example of a PGM is PGM from *Thermococcus kodakaraensis* (Uniprot ID Q68BJ6), disclosed in International Patent Application Publication WO2017/059278; or PGM from *Caldibacillus debilis* (Uniprot A0A150LLZ1), disclosed in PCT Application Publication 2020/092315.

Figure 2:
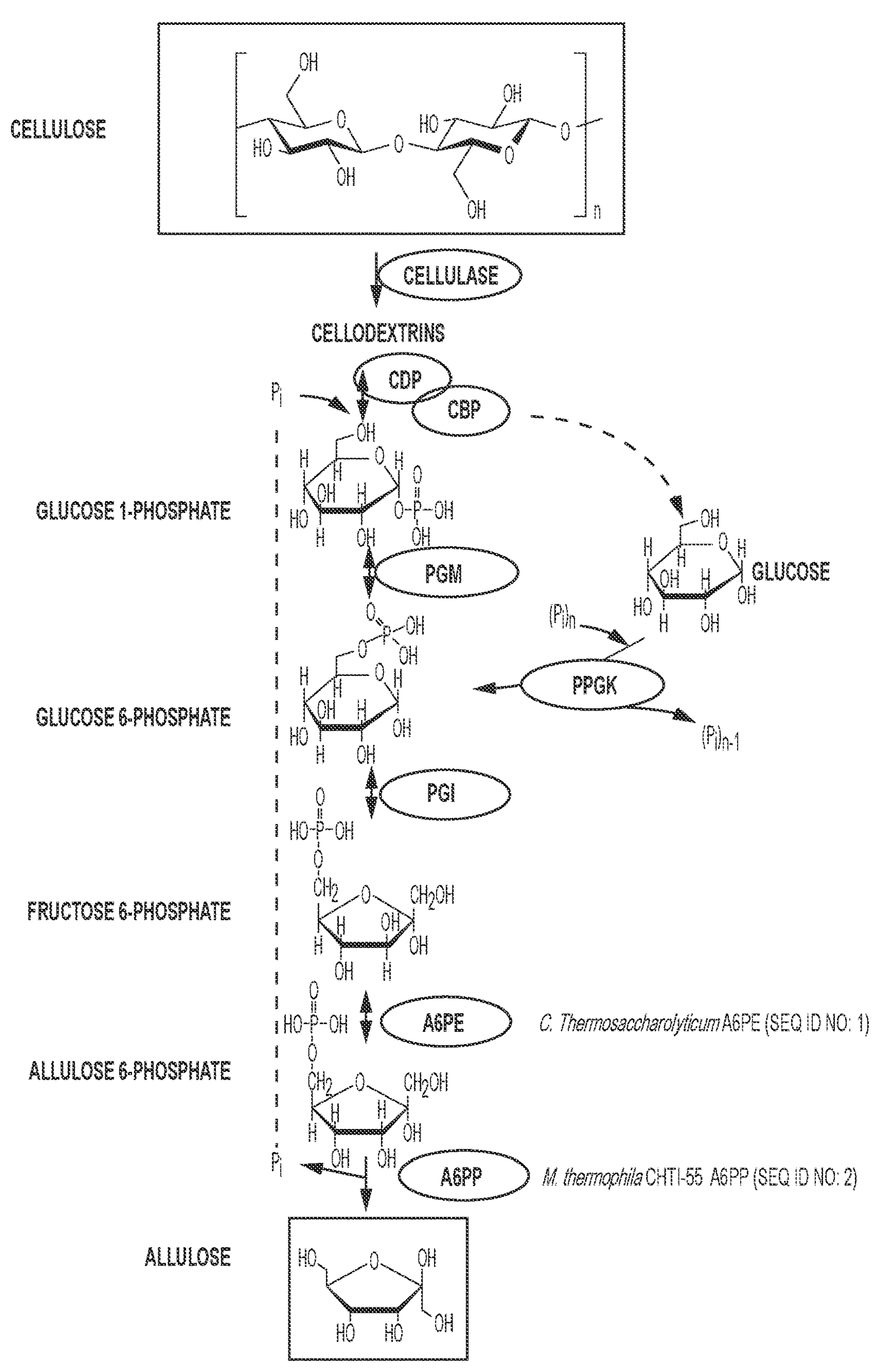
FIG. 2 shows an enzymatic pathway converting cellulose or its derived products to allulose. CDP, cellodextrin phosphorylase; CBP, cellobiose phosphorylase; PPGK, polyphosphate glucokinase; PGM, phosphoglucomutase; PGI, phosphoglucoisomerase; A6PE, allulose 6-phosphate epimerase; A6PP, allulose 6-phosphate phosphatase. In processes of the invention, the A6PE comprises an amino acid sequence having at least 90% sequence identity to SEQ ID NO: 1, and/or the A6PP comprises an amino acid sequence having at least 90% sequence identity to SEQ ID NO: 2.
Figure 3:
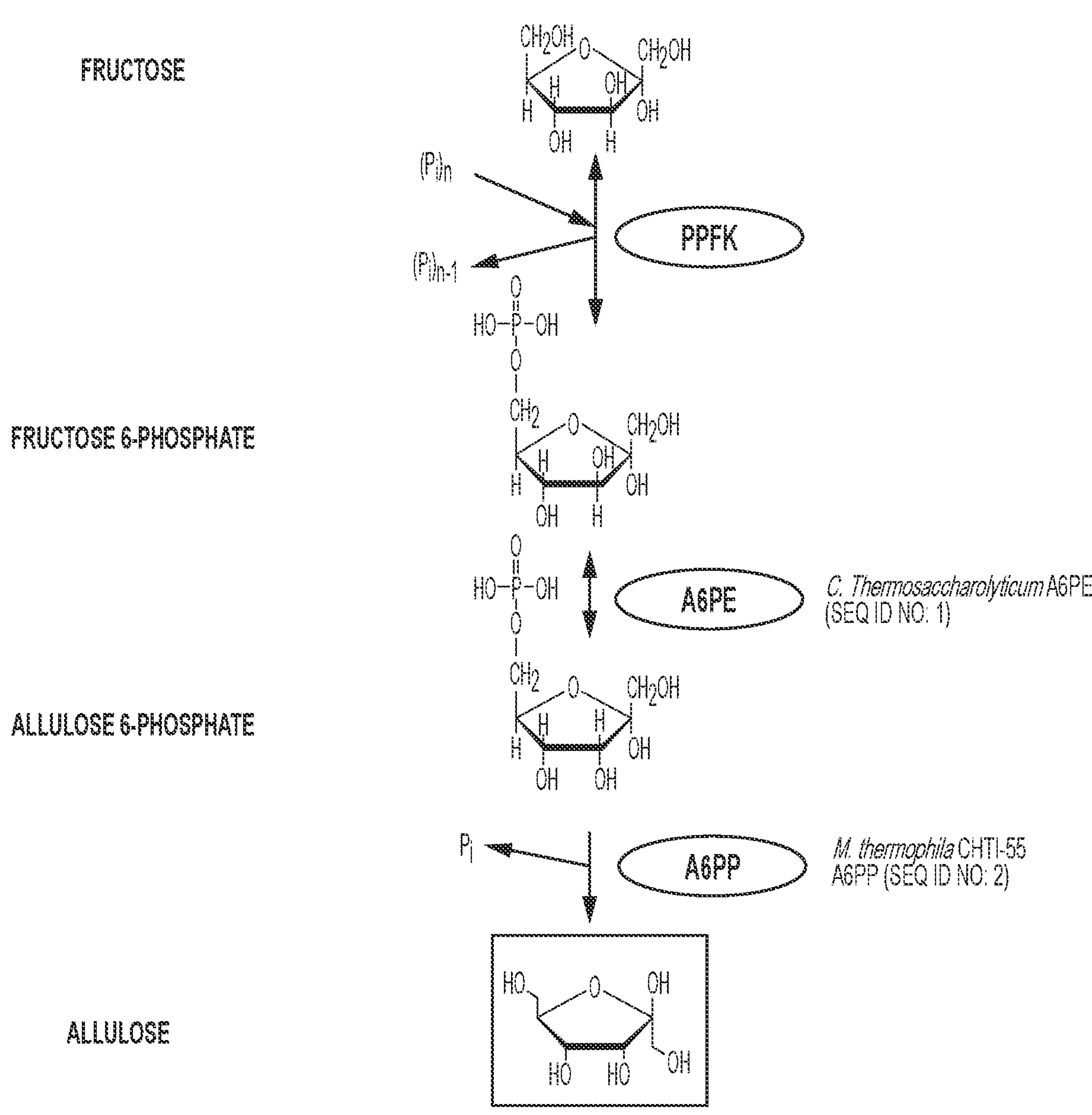
FIG. 3 is a schematic diagram illustrating an enzymatic pathway converting fructose to allulose. PPFK, polyphosphate fructokinase; A6PE, allulose 6-phosphate epimerase; A6PP, allulose 6-phosphate phosphatase. In processes of the invention, the A6PE comprises an amino acid sequence having at least 90% sequence identity to SEQ ID NO: 1, and/or the A6PP comprises an amino acid sequence having at least 90% sequence identity to SEQ ID NO: 2.
Figure 4:
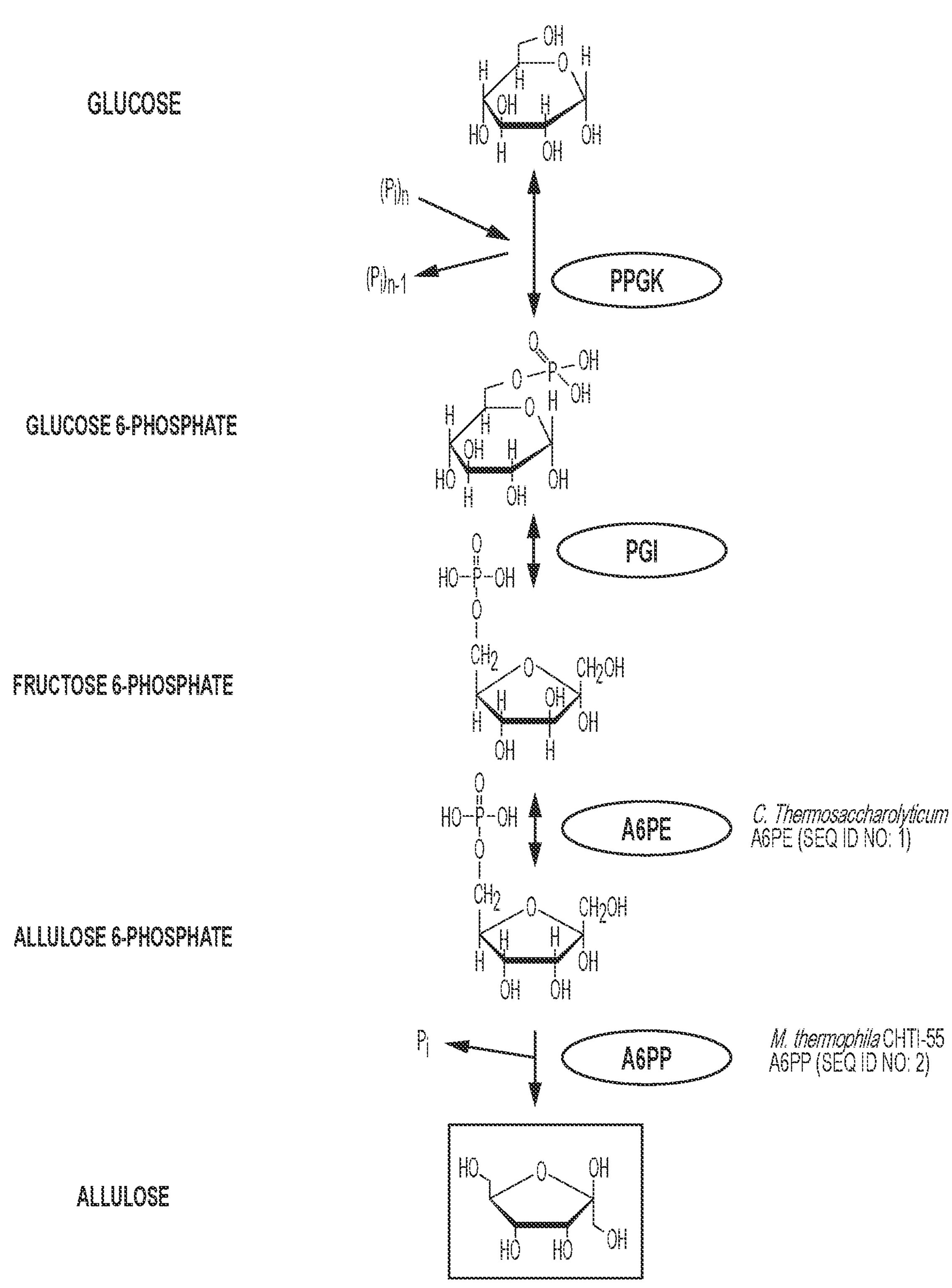
FIG. 4 is a schematic diagram illustrating an enzymatic pathway converting glucose to allulose. PPGK, polyphosphate glucokinase; PGI, phosphoglucoisomerase; A6PE, allulose 6-phosphate epimerase; A6PP, allulose 6-phosphate phosphatase. In processes of the invention, the A6PE comprises an amino acid sequence having at least 90% sequence identity to SEQ ID NO: 1, and/or the A6PP comprises an amino acid sequence having at least 90% sequence identity to SEQ ID NO: 2.
Figure 5:
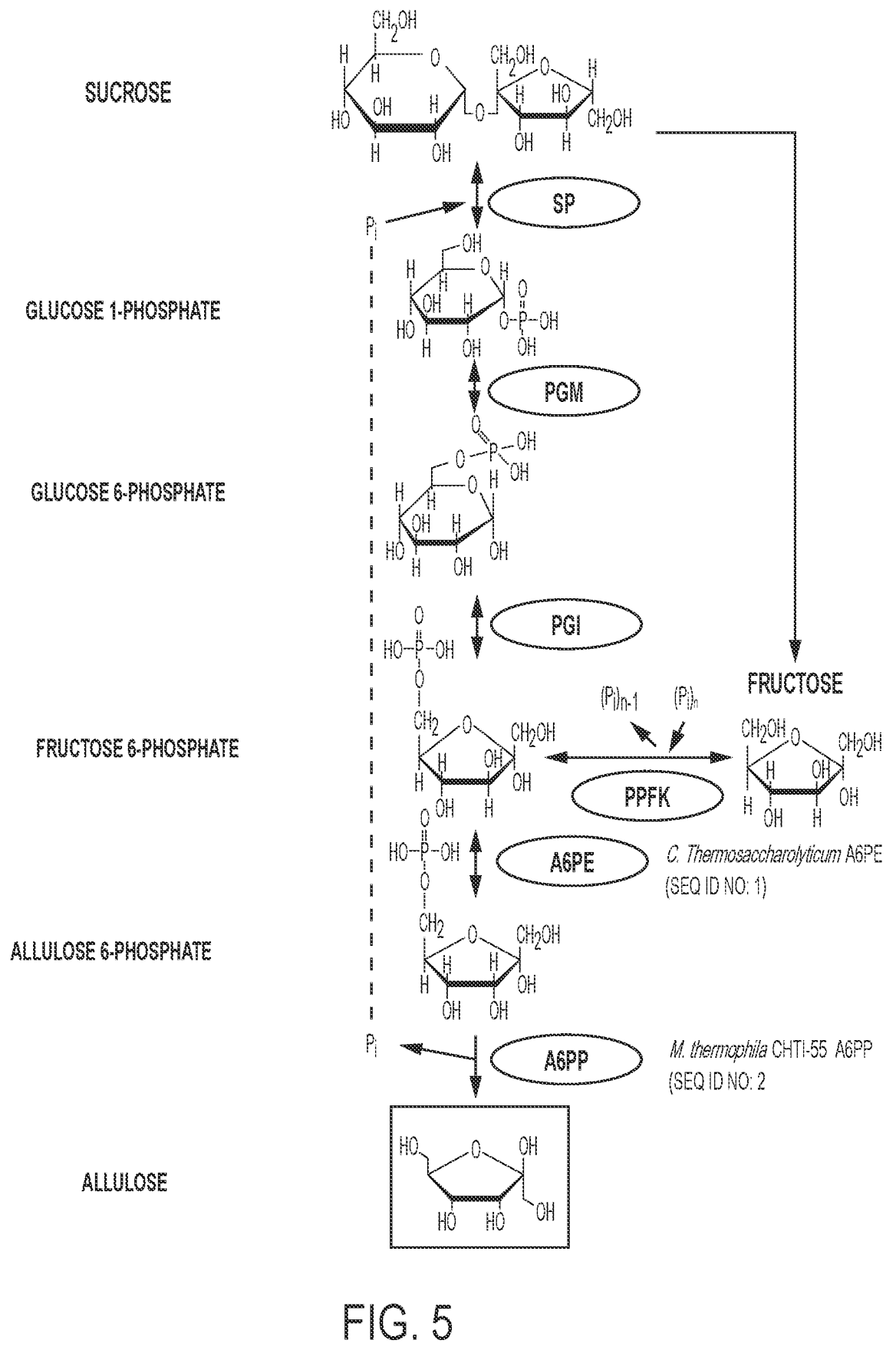

Some improved processes of the invention also include a step of converting a saccharide to the G1P, using at least one enzyme. For example, an improved process may convert a saccharide selected from a starch or derivative thereof, as described in FIG. 1, cellulose or a derivative thereof, as described in FIG. 2, fructose, as described in FIG. 3, glucose, as described in FIG. 4, or sucrose, as described in FIG. 5. The enzyme or enzymes used in the step of converting a saccharide to the G1P in such improved processes of the invention may be, for example, alpha-glucan phosphorylase (αGP), maltose phosphorylase, sucrose phosphorylase, cellodextrin phosphorylase, cellobiose phosphorylase, and/or cellulose phosphorylase, and mixtures thereof. The choice of the enzyme or enzyme combination to arrive at F6P depends on the saccharide used in the process.

Cellulose is the most abundant bioresource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

In some improved processes of the invention, cellulose and its derived products may be converted to allulose by a series of enzymatic steps, including: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to allulose as described above, and the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase). Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partial hydrolysis by using concentrated acids, including hydrochloric acid, sulfuric acid, phosphoric acid and their combinations.

When the saccharides include cellobiose, and the enzymes contain cellobiose phosphorylase, G1P is generated from cellobiose and phosphate by cellobiose phosphorylase. When the saccharides contain cellodextrins and the enzymes include cellodextrin phosphorylase, G1P is generated from cellodextrins and phosphate by cellodextrin phosphorylase. When the saccharides include cellulose, and enzymes contain cellulose phosphorylase, the G1P is generated from cellulose and phosphate by cellulose phosphorylase.

When the saccharides include maltose and the enzymes contain maltose phosphorylase, the G1P is generated from maltose and phosphate by maltose phosphorylase. If the saccharides include sucrose, and enzymes contain sucrose phosphorylase, the G1P is generated from sucrose and phosphate by sucrose phosphorylase.

When the saccharide is starch or a starch derivative, the derivative may be selected from the group consisting of amylose, amylopectin, soluble starch, amylodextrin, maltodextrin, maltose, maltotriose, and glucose, and mixtures thereof. In certain processes of the invention, the enzymes used to convert a saccharide to G1P contain αGP. In this step, when the saccharides include starch, the G1P is generated from starch and phosphate by αGP; when the saccharides contain soluble starch, amylodextrin, or maltodextrin, the G1P is produced from soluble starch and phosphate, amylodextrin and phosphate, or maltodextrin and phosphate by αGP. An example of αGP is αGP from *Thermotoga maritima* (Uniprot ID G4FEH8), disclosed in International Patent Application Publication WO2017/059278; or αGP from *Thermus* sp. CCB_US3_UF1 (Uniprot G8NCC0), disclosed in International Patent Application Publication 2020/092315.

Some processes according to the invention may further comprise the step of converting starch to a starch derivative, where the starch derivative is prepared by enzymatic hydrolysis of starch or by acid hydrolysis of starch. In certain processes of the invention, maltose phosphorylase (MP) can be used to increase allulose yields by phosphorolytically cleaving the degradation product maltose into G1P and glucose. Alternatively, 4-glucan transferase (4GT) can be used to increase allulose yields by recycling the degradation products glucose, maltose, and maltotriose into longer maltooligosaccharides; which can be phosphorolytically cleaved by αGP to yield G1P. An example of 4GT is 4GT from *Thermococcus litoralis* (Uniprot ID 032462), disclosed in International Patent Application Publication WO2017/059278; or 4GT from *Anaerolinea thermophila* strain DSM 14523 (Uniprot E8MXP8), disclosed in International Patent Application Publication 2020/092315. In some processes of the invention, polyphosphate and polyphosphate glucokinase (PPGK) can be added to the process, thus increasing yields of allulose by phosphorylating the degradation product glucose to G6P.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

Where the processes use a starch derivative, the starch derivative can be prepared by enzymatic hydrolysis of starch catalyzed by isoamylase, pullulanase, α-amylase, or their combination. Corn starch contains many branches that impede αGP action. Isoamylase and pullulanase can be used to de-branch starch, yielding linear amylodextrin. Isoamylase-pretreated and pullulanase-pretreated starch can result in a higher F6P concentrations in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to allulose.

Allulose can also be produced from fructose. See FIG. 3. Processes according to the inventions can also comprise the step of converting fructose to F6P, wherein the step is catalyzed by at least one enzyme and, optionally, the step of converting sucrose to the fructose, wherein the step is catalyzed by at least one enzyme. For example, the process involves generating F6P from fructose and polyphosphate catalyzed by polyphosphate fructokinase (PPFK). The conversion of F6P to allulose is described above. The fructose can be produced, for example, by an enzymatic conversion of sucrose. The phosphate ions generated when A6P is converted to allulose can then be recycled in the steps of converting sucrose to G1P.

Allulose can also be produced from glucose. See FIG. 4. Processes according to the inventions can also comprise the step of converting glucose to G6P, catalyzed by at least one enzyme, and, optionally, the step of converting sucrose to the fructose, wherein the step is catalyzed by at least one enzyme. For example, the process involves generating G6P from glucose and polyphosphate catalyzed by polyphosphate glucokinase (PPGK). The glucose can be produced, for example, by 4-glucan transferase recycling of maltotriose to longer chain maltodextrins.

In some methods of the invention, the phosphate ions generated when A6P is converted to allulose are recycled in the step of converting starch derivatives to G1P (See, e.g., FIG. 1), cellulose derivatives to G1P (See e.g., FIG. 2), or sucrose to G1P (See FIG. 5), especially if the process is conducted in a single reaction vessel. Additionally, PPFK and polyphosphate can be used to increase allulose yields by producing F6P from fructose generated by the phosphorolytic cleavage of sucrose by SP.

Processes for preparing allulose from a saccharide, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to A6P via allulose 6-phosphate epimerase (A6PE), and (v) converting A6P to allulose via allulose 6-phosphate phosphatase (A6PP). In improved processes of the invention, the A6PE comprises an amino acid sequence having at least 90% sequence identity to SEQ ID NO: 1, and/or the A6PP comprises an amino acid sequence having at least 90% sequence identity to SEQ ID NO: 2. In such processes, for example, the enzyme in step (i) is αGP. Typically, the ratios of enzyme units used in the process are 1:1:1:1:1 (αGP:PGM:PGI:A6PE:A6PP). An enzyme unit is the amount of enzyme needed to convert 1 umol of substrate to product in 1 minute. Accordingly, an enzyme with a higher activity will have a lower amount of enzyme, in terms of mg of enzyme per one enzyme unit, compared to an enzyme with a lower activity which catalyzes the same reaction. To optimize product yields, these ratios can be adjusted in any number of combinations. For example, a particular enzyme may be present in an amount about 2×, 3×, 4×, 5×, etc. relative to the amount of other enzymes.

A process for preparing allulose according to the invention may include the following additional steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Processes to prepare allulose according the invention can be conducted in a single bioreactor or reaction vessel. Alternatively, the steps can also be conducted in a plurality of bioreactors, or reaction vessels, that are arranged in series.

In a preferred process, the enzymatic production of allulose is conducted in a single reaction vessel.

The enzymes used in the invention may take the form of soluble, immobilized, assembled, or aggregated proteins. These enzymes could be adsorbed on insoluble organic or inorganic supports commonly used to improve functionality, as known in the art. These include polymeric supports such as agarose, methacrylate, polystyrene, phenol-formaldehyde, or dextran, as well as inorganic supports such as glass, metal, or carbon-based materials. These materials are often produced with large surface-to-volume ratios and specialized surfaces that promote attachment and activity of immobilized enzymes. The enzymes might be affixed to these solid supports through covalent, ionic, or hydrophobic interactions. The enzymes could also be affixed through genetically engineered interactions such as covalent fusion to another protein or peptide sequence with affinity to the solid support, most often a poly-histidine sequence. The enzymes might be affixed either directly to the surface or surface coating, or they might be affixed to other proteins already present on the surface or surface coating. The enzymes can be immobilized all on one carrier, on individual carriers, or a combination of the two (e.g., two enzyme per carrier then mix those carriers). These variations can be mixed evenly or in defined layers to optimize turnover in a continuous reactor. For example, the beginning of the reactor may have a layer of αGP to ensure a high initial G1P increase. Enzymes may be immobilized all on one carrier, on individual carriers, or in groups. These enzymes may be mixed evenly or in defined layers or zones to optimize turnover.

Any suitable biological buffer known in the art can be used in an improved process of the invention, such as HEPES, PBS, BIS-TRIS, MOPS, DIPSO, Trizma, phosphate buffer, etc. The reaction buffer for all embodiments can have a pH ranging from 4.0-9.0. More preferably, the reaction buffer pH can range from about 6.0 to about 7.8. For example, the reaction buffer pH can be 6.0, 6.2, 6.4, 6.6, 6.8, 7.0, 7.2, 7.3, 7.4, 7.5, 7.6, 7.7, or 7.8.

In some improved processes of the invention the reaction buffer contains divalent metal cations. Examples include $Mn^{2+}$, $Co^{2+}$, $Mg^{2+}$ and $Zn^{2+}$, and the like, preferably $Co^{2+}$ and $Mg^{2+}$. The concentration of divalent metal cations can range from about 0 mM to about 150 mM, from about 0 mM to about 100 mM, from about 1 mM to about 50 mM, preferably from about 5 mM to about 50 mM, or more preferably from about 10 mM to about 50 mM. For instance, the divalent metal cation concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

The reaction temperature at which improved process steps are conducted can range from 37-85° C. More preferably, the steps are conducted at a temperature ranging from about 37° C. to about 85° C. The temperature can be, for example, about 40° C., about 45° C., about 50° C., about 55° C., or about 60° C. Preferably, the reaction temperature is about 50° C. In some improved processes of the invention, the reaction temperature is constant, and is not changed during the process.

The reaction time of the disclosed processes can be adjusted as necessary and can range from about 0.5 hour to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The steps in an improved process of the invention may run in batch or in a continuous process using a packed bed reactor or similar device. In a continuous process, a solution maltodextrin would be pumped through a bed of immobilized enzyme at such a rate that conversion to allulose would be complete when the solution leaves the column for downstream processing. For example, 200 g/L of maltodextrin can be pumped through a column packed with immobilized enzymes (maintained at, for example, 50° C.) such that when the maltodextrin leaves the column maximum allulose yield is achieved. This methodology offers greater volumetric productivity over batch methods. This limits the time our product is in contact with the column and reaction conditions, which decreases chances of product degradation (e.g., potential hydroxymethylfurfural formation). Whether in batch or continuous mode the various steps of processes of the invention may be conducted using the same reaction conditions as the other steps. For example, in a particular process of the invention using a single bioreactor or reaction vessel, the reaction conditions such as pH and temperature, and reaction buffer are kept constant for all steps of the process.

Phosphate ions produced by A6PP dephosphorylation of A6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the allulose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentrations result in decreased production costs due to low total phosphate and thus lowered cost of phosphate removal. It also prevents inhibition of A6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(H), i.e., NAD(H)-free. Other advantages also include the fact that at least one step of the disclosed processes for making allulose involves an energetically favorable chemical reaction. While the use of enzymes with higher activities will not affect the overall energetics, the ability to use lower amounts of enzymes in the improved processes is advantageous. The advantage is the reduction of the overall cost of enzyme in the total production cost of the product.

The processes according to the invention can achieve high yields due to the very favorable equilibrium constant for the overall reaction. Theoretically, up to 99% yields can be achieved if the starting material is completely converted to an intermediate. Also, the step of converting A6P to allulose according to the invention is an irreversible phosphatase reaction, regardless of the feedstock. Therefore, allulose is produced with a very high yield.

Processes of the invention use low-cost starting materials and reduce production costs by decreasing costs associated with the feedstock and product separation. Starch and its derivatives, cellulose and its derivatives, and sucrose are less expensive feedstocks than, for example, crystalline fructose. When allulose is produced from fructose, the yield is only ~28% (WO 2016/160573). Fructose and allulose are then separated via chromatography, which together leads to higher production costs than the disclosed method.

Processes according to the invention allow for easy recovery of allulose, and separation costs are minimized. Preferably, in processes of the invention, the recovery of allulose is not via chromatographic separation. Following production of allulose in a continuous reaction, the product is instead passed through ultrafiltration, ion exchange (cation then anion, not mixed bed), concentration, crystallization, crystal isolation, and drying. Due to high yields of allulose, the crystallization step is all that is needed to purify allulose. To further purify allulose prior to crystallization, one can employ ultrafiltration to eliminate the risk of enzyme being present in the crystallization process or nanofiltration to remove any unconverted dextrins that may co-crystallize with allulose or limit the recyclability of the mother liquor (maltodextrin, maltotetraose, maltotriose, maltose, etc.).

An improved process for preparing allulose according to the invention includes the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to A6P via allulose 6-phosphate epimerase (A6PE), and (v) converting A6P to allulose via allulose 6-phosphate phosphatase (A6PP), where the A6PE comprises an amino acid sequence having at least 90% sequence identity to SEQ ID NO: 1, and/or where the A6PP comprises an amino acid sequence having at least 90% sequence identity to SEQ ID NO: 2. This process is preferably conducted in a single bioreactor or reaction vessel.

Preferably, an improved process for preparing allulose according to the invention includes the following steps: (i) converting a saccharide to glucose 1-phosphate (G1P) using αGP, where the saccharide is selected from the group consisting of starch, one or more derivatives of starch, or a combination thereof; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to A6P via allulose 6-phosphate epimerase (A6PE), and (v) converting A6P to allulose via allulose 6-phosphate phosphatase (A6PP), where the A6PE comprises an amino acid sequence having at least 90% sequence identity to SEQ ID NO: 1, and/or where the A6PP comprises an amino acid sequence having at least 90% sequence identity to SEQ ID NO: 2. The process is preferably conducted in a single reactor vessel and may incorporate one or more of the various process conditions discussed above.

EXAMPLES

Materials and Methods All chemicals, including glucose 1-phosphate, magnesium chloride, sodium phosphate (mono and dibasic), are reagent grade or higher and purchased from Sigma-Aldrich (St. Louis, MO, USA) or Fisher Scientific (Pittsburgh, PA, USA), unless otherwise noted. *E. coli* BL21 (DE3) (Sigma-Aldrich, St. Louis, MO, USA) was used as a host cell for recombinant protein expression. ZYM-5052 media containing 50 mg L−1 kanamycin was used for *E. coli* cell growth and recombinant protein expression.

Production and purification of recombinant enzymes The *E. coli* BL21 (DE3) strain harboring a protein expression plasmid (pET28a) was incubated in a 1 L Erlenmeyer flask with 100 mL of ZYM-5052 media containing 50 mg $L^{-1}$ kanamycin. Cells were grown at 37° C. with rotary shaking at 220 rpm for 16-24 hours. The cells were harvested by centrifugation at 12° C. and washed once with either: 20 mM HEPES (pH 7.5) containing 50 mM NaCl and 5 mM $MgCl_2$ for heat precipitation; or 20 mM HEPES (pH 7.5) containing 300 mM NaCl and 5 mM imidazole for Ni purification. The cell pellets were resuspended in the same buffer, and lysed by sonication. After centrifugation, the target proteins in the supernatants were purified. His-tagged proteins were purified by the Profinity IMAC Ni-Charged Resin (Bio-Rad, Hercules, CA, USA). The amount of protein purified was quantified by absorbance at 280 nm and used for the relative expression yield calculations in Table 1.

Heat Stability The *E. coli* BL21 (DE3) strain harboring a protein expression plasmid (pET28a) was incubated in a 1-L Erlenmeyer flask with 100 mL of ZYM-5052 media containing 50 mg $L^{-1}$ kanamycin. Cells were grown at 37° C. with rotary shaking at 220 rpm for 16-24 hours. The cells were harvested by centrifugation at 12° C. and washed once with either 20 mM HEPES (pH 7.5) containing 50 mM NaCl and 5 mM $MgCl_2$. The cell pellets were re-suspended in the same buffer and lysed by sonication. After centrifugation, the target proteins in the supernatants were tested for heat stability at 50-80° C. for 30 minutes. The stability of the recombinant proteins was examined by sodium dodecyl sulfate polyacrylamide gel electrophoresis (SDS-PAGE) and recorded by visual inspection, as described in Table 1.

TABLE 1

| A6PE UniProt ID | Heat Stability | Relative Expression Yield |
|---|---|---|
| D9TQJ4 | Untested due to low yields | 20.6% |
| A0A090IXZ8 | Untested due to low yields | 27.8% |
| P32719 | Untested due to mesophilic nature | 54.6% |
| A8UV28 | Untested due to lack of activity | 86.5% |
| UPI000411882A | 90% soluble after 30 minutes at 60° C. | 81.6% |
| G7M2I3 | 60% soluble after 30 minutes at 50° C. | 93.6% |
| A0A094WLM1 | 50% soluble after 30 minutes at 50° C. | 134% |
| A0A223HZI7 | 80% soluble after 30 minutes at 60° C. | 100% |

Example 1. Assessing relative activity for the allulose 6-phosphate epimerase (A6PE)-dependent conversion of G1P to allulose in an improved process. The conversion of G1P to allulose by an enzymatic process including an A6PE with an amino acid sequence of UniProt ID A0A223HZI7 ("the A0A223HZI7 A6PE") was compared to G1P to allulose conversion processes, which differed only with respect to the A6PE used in each process. More particularly, the G1P to allulose conversion was compared using processes, which included: a PGM with the amino acid sequence of UniProt ID A0A150LLZ1; a PGI with an amino acid sequence of UniProt ID Q5SLL6; the A0A223HZI7 A6PE or an A6PE with the amino acid sequence of either UniProt ID D9TQJ4, UniProt ID A0A090IXZ8, UniProt ID A8UV28, UniProt ID G7M213, UniProt ID A0A094WLM1, Uniparc ID UPI000411882A, or Uniprot P32719 (the P32719 enzyme is unstable at 50° C.); and an A6PP with an amino acid sequence of Uniprot ID A0A0E3NCH4. Each process was performed in 0.20 mL reaction mixturesaaa containing 38.5 mM G1P, 50 mM HEPES pH 7.2, 15 mM $MgCl_2$, 0.5 mM $CoCl_2$, 0.05 g/L PGM, 0.05 g/L PGI, 0.025 g/L A6PE, and 0.15 g/L A6PP. The reactions were incubated at 50° C. for 3 hours. A6PE was the rate limiting enzyme in the conversion of G1P to allulose. The reactions were stopped via enzyme filtration using a Vivaspin® 2 concentrator (10,000 MWCO), and analyzed by HPLC (Agilent 1100 series) using an Agilent Hi-Plex H column and a refractive index detector. The sample runs were in 5 mM $H_2SO_4$ at 0.6 mL/min for 15.5 minutes at 65° C.

Results showed no significant A6PE-dependent differences in activity, with the exception that the A6PE with the UniProt A8UV28 amino acid sequence was not active under the conditions tested.

Example 2. Assessing lower allulose 6-phosphate epimerase (A6PE)-dependent allulose to fructose conversion activity. The conversion of allulose to fructose by an enzymatic process including the A0A223HZI7 A6PE was compared to allulose to fructose conversion processes which differed only with respect to the A6PE used in each process. More specifically, the allulose to fructose conversion was compared using processes which included the A0A223HZI7 A6PE or an A6PE with the amino acid sequence of either UniProt ID D9TQJ4, UniProt ID A0A090IXZ8, UniProt ID G7M213, UniProt ID A0A094WLM1, UniProt ID A0A223HZI7, or UniParc ID UPI000411882A (the A6PEs with amino acid sequences of UniProt ID P32719 and UniProt ID A8UV28 were omitted due to incompatibility with the pathway). Each process was performed in 0.20 mL reaction mixtures containing 200 g/L allulose, 10 mM HEPES pH 7.2, 5 mM $MgCl_2$, 0.5 mM $CoCl_2$, and 0.025 g/L or 0.25 g/L A6PE. The reactions were incubated at 50° C. for 6 hours. The reactions were stopped via filtration of enzyme with a Vivaspin 2 concentrator (10,000 MWCO) and analyzed via HPLC (Agilent 1100 series) using a SupelCogel Pb-column and refractive index detector. The sample runs were in ultrapure water at 0.6 mL/min for 40 minutes at 80° C.

Results, summarized in Table 2, indicated the tested A6PEs produced relatively little fructose from allulose with the exception of enzymes with the amino acid sequences of UniProt ID A0A090IXZ8 and UniParc ID UPI000411882A. Notably, no conversion of allulose to fructose was observed for the A0A223HZI7 A6PE at an enzyme composition of 0.025 g/L

TABLE 2

| A6PE UniProt ID | Conversion to fructose at 0.025 g/L | Conversion to fructose at 0.25 g/L |
|---|---|---|
| D9TQJ4 | 0.1% | 0.3% |
| A0A090IXZ8 | 1.2% | 44.2% |
| P32719 | Untested due to mesophilic nature | |
| A8UV28 | Untested due to lack of activity | |
| UPI000411882A | 0.6% | 6.7% |
| G7M2I3 | 0.1% | 1.0% |
| A0A094WLM1 | 0.1% | 2.1% |
| A0A223HZI7 | 0% | 1.0% |

Example 3. Assessing relative activity of an allulose 6-phosphate epimerase (A6PE) with improved properties in the conversion of maltodextrin to allulose. The full-cascade conversion of maltodextrin to allulose by an enzymatic process including the A0A223HZI7 A6PE (which demonstrated no fructose-from-allulose activity) was compared to maltodextrin to allulose conversion processes, which differed only with respect to the A6PE used in each process, to determine how F6PEs with differing fructose-from-allulose activities affect allulose yield. More specifically, the maltodextrin to allulose conversion was compared using processes which included: an αGP with an amino acid sequence of UniProt ID G8NCC0; a PGM with an amino acid sequence of UniProt ID A0A150LLZ1; a PGI with an amino acid sequence of UniProt ID Q5SLL6; the A0A223HZI7 A6PE or an A6PE with an amino acid sequence of either UniProt ID A0A090IXZ8 (which demonstrated high fructose-from-allulose activity) or UniParc ID UPI000411882A (which demonstrated moderate fructose-from-allulose activity); an A6PP with an amino acid sequence of UniProt ID A0A0E3NCH4; and a 4GT with an amino acid sequence of UniProt ID E8MXP8. Each process was performed in 0.20 mL reaction mixtures containing 100 g/L debranched Sigma Aldrich maltodextrin DE 4-7, 25 mM sodium phosphate pH 7.2, 15 mM $MgCl_2$, 0.5 mM $CoCl_2$, 0.3 g/L αGP, 0.075 g/L PGM, 0.075 g/L PGI, 0.1 g/L A6PE, 0.1 g/L A6PP, and 0.04 g/L 4GT. The reactions were incubated at 50° C. for 18 hours such that the reaction was not fully complete at the time of analysis. The reaction were stopped via filtration of enzyme with a Vivaspin® 2 concentrator (10,000 MWCO) and analyzed via HPLC (Agilent® 1100 series) using a Supel-Cogel® Pb-column and refractive index detector. The sample runs were in ultrapure water at 0.6 mL/min for 40 minutes at 80° C.

Figure 6:
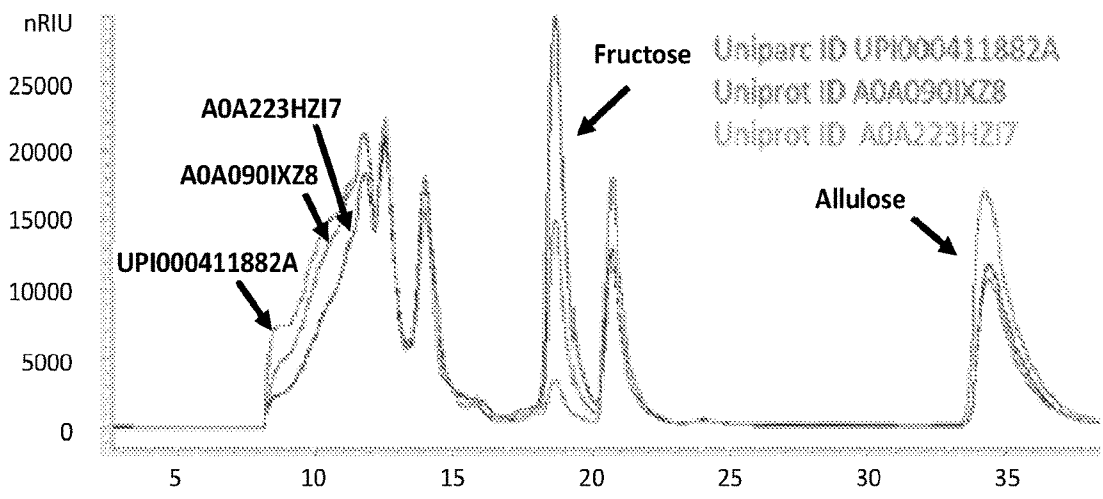
FIG. 6 shows the conversion of maltodextrin to allulose measured by HPLC. The following enzymes were used: αGP (Uniprot ID G8NCC0), PGM (Uniprot ID A0A150LLZ1), PGI (Uniprot ID Q5SLL6), A6PP (Uniprot ID A0A0E3NCH4), and 4GT (Uniprot ID E8MXP8). A6PEs (Uniprot IDs A0A090IXZ8) and (Uniparc ID UPI000411882A) were compared with an A6PE used in the improved processes of the invention (A0A223HZI7).
Figure 7:
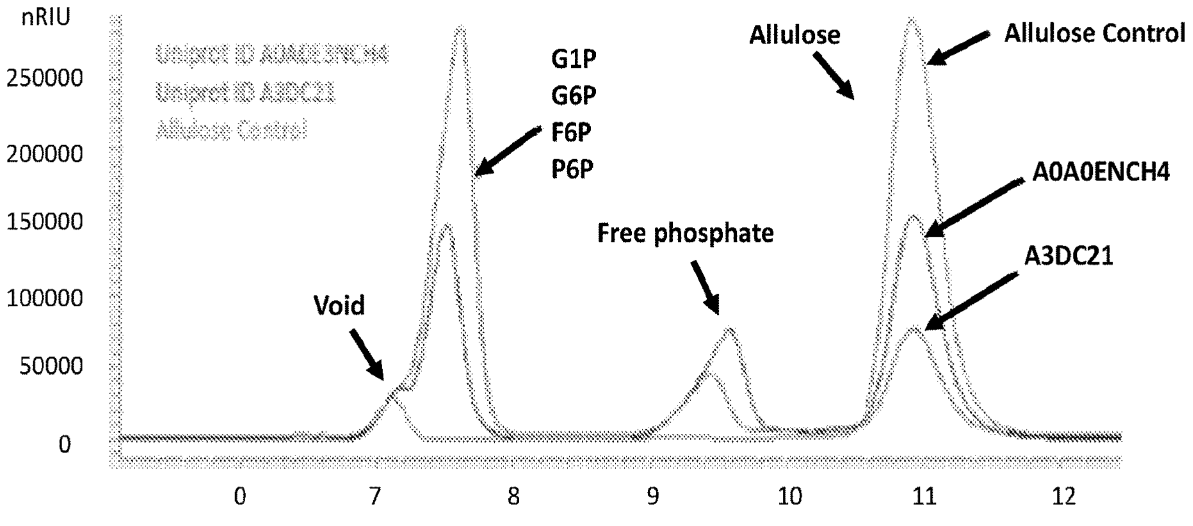
FIG. 7 shows the conversion of G1P to allulose measured by HPLC. The following enzymes were used: PGM (Uniprot ID A0A150LLZ1), PGI (Uniprot ID Q5SLL6), and A6PE (Uniprot ID D9TQJ4). A6PP (Uniprot ID A3DC21) was compared with an A6PP used in the improved processes of the invention, (Uniprot ID A0A0E3NCH4).

Results, illustrated in FIG. 6, showed that the process involving the A6PE with the amino acid sequence of UniParc ID UPI000411882A produced substantially more fructose than that involving the A0A223HZI7 A6PE. As expected, the process involving the A6PE with the amino acid sequence of UniProt ID A0A090IXZ8 produced an intermediary amount of fructose. The process involving the A0A223HZI7 A6PE produced the most allulose in 18 hours. This resulted in the highest allulose yield pathway, and one more efficient than any previously disclosed for producing allulose using an A6PE. The relative affinities for F6P/A6P versus allulose for a given A6PE enzyme is demonstrated by the observed differences between fructose-from-allulose activity versus allulose-from-maltodextrin cascade. For example, while the A6PE with the amino acid sequence of UniProt ID A0A090IXZ8 produced mucher higher amounts of fructose when from allulose alone compared to the A6PE with the amino acid sequence of Uniparc ID UPI000411882A, in a full cascade reaction the A6PE with the amino acid sequence of Uniprot ID A0A090IXZ8 performs better since F6P/A6P are able to out compete allulose more efficiently for this enzyme than for the A6PE with the amino acid sequence of Uniparc ID UPI000411882A.

Example 4. Assessing relative activity of an allulose 6-phosphate phosphatase (A6PP) with improved properties in the conversion of G1P to allulose. The conversion of G1P to allulose by an enzymatic process using an A6PP with the amino acid sequence of UniProt ID A0A0E3NCH4 ("the A0A0E3NCH4 A6PP") was compared to G1P to allulose conversion processes which differed only with respect to the A6PP used in each process. More specifically, the G1P to allulose conversion was compared using processes which included: a PGM with the amino acid sequence of UniProt ID A0A150LLZ1; a PGI with the amino acid sequence of UniProt ID Q5SLL6; an A6PE with the amino acid sequence of UniProt ID D9TQJ4; and either the the A0A0E3NCH4 A6PP or an A6PP with the amino acid sequence of UniProt ID A3DC21. The previously disclosed A6PPs with amino acid sequences of either Uniprot ID Q5LGR4 or Uniprot ID Q89ZR1 could not be included in the comparison because these enzymes are unstable at 50° C. Each process was performed in 0.20 mL reaction mixtures containing 38.5 mM G1P, 50 mM HEPES pH 7.2, 0.5 mM $CoCl_2$, 0.05 g/L PGM, 0.05 g/L PGI, 0.025 g/L A6PE, and 0.05 g/L A6PP. The reactions were incubated at 50° C. for 3 hours. A6PP was the rate limiting enzyme in the conversion of G1P to allulose. The reactions were stopped via filtration of enzymes using a Vivaspin® 2 concentrator (10,000 MWCO) and analyzed via HPLC (Agilent 1100 series), using an Agilent Hi-Plex® H-column and refractive index detector. The samples runs were in 5 mM $H_2SO_4$ at 0.6 mL/min for 15.5 minutes at 65° C. Results, summarized in Table 3, showed a 2.2-fold improvement in allulose production using the A0A0E3NCH4 A6PP relative to the process using the previously disclosed A6PP with the amino acid sequence of UniProt ID A3DC21.

TABLE 3

| A6PP Uniprot ID | Relative activity at 50° C. (%) |
|---|---|
| A3DC21 | 100 |
| Q5LGR4 | N/A |
| Q89ZR1 | N/A |
| A0A0E3NCH4 | 220 |

SEQUENCE LISTING

A6PE;
UniProt ID A0A223HZI7;
SEQ ID NO: 1
*Thermoanaerobacterium thermosaccharolyticum*

MKPMFAPSLMCANFLDLKNQIEILNERADIYHIDI

MDGHYVKNFALSPYLMEQLKTIAKIPMDAHLMVEN

PADFLECIAKSGATYISPHAETINKDAFRIMRTIK

ALGCKTGIVLNPATPVEYIKYYIGMLDKITILTVD

AGFAGQTFINEMLDKIAEIKSLRDQNGYSYLIEVD

GSCNEKTFKQLAEAGTDVFVVGSSGLFNLDTDLKV

AWDKMMDTFTRCTSN;

A6PP;
UniProt ID A0A0E3NCH4;
*Methanosarcina thermophila*
SEQ ID NO: 2

MLKALIFDMDGVLVDSMPFHAAAWKKAFFEMGMEI

QDSDIFAIEGSNPRNGLPLLIRKARKEPEAFDFEA

ITSIYRQEFKRVFEPKAFEGMKECLEVLKKRFLLS

VVSGSDHVIVHSIINRLFPGIFDIVVTGDDIINSK

PHPDPFLKAVELLNVRREECVVIENAILGVEAAKN

ARIYCIGVPTYVEPSHLDKADLVVEDHRQLMQHLL

SLEPANGFRQ;

A6PE;
UniProt ID D9TQJ4;
*Thermoanaerobacterium thermosaccharolyticum*
SEQ ID NO: 3

MKYLFSPSLMCMNLIKLNEQISVLNSKADFLHVDI

MDGHFVKNITLSPFFIEQIKSYVNIPIDAHLMVEN

PGDYIEICEKSGASFITIHAETINREAFRIIDRIK

SHGLMVGIALNPATPISEIKHYINKIDKITIMTVD

PGFAGQPFIPEVLEKIRDLKRLKDDNNYNYLIEAD

GSCNKNTFQVLKDAGCKVFVLGSSGLFNLSDDLGK

AWEIMIGNFNG;

A6PE;
UniProt ID A0A090IXZ8;
*Bacillus thermoamylovorans*
SEQ ID NO: 4

MSNKIEFSPSLMTMDLDKFKEQITFLNNHVGSYHI

DIMDGHYVPNITLSPWFVQEVRKISDVPMSAHLMV

TNPSFWVQQLIDIKCEWICMHVETLDGLAFRLIDQ

-continued

IHDAGLKAGVVLNPETSVDAIRPYIDLVDKVTIMT

VDPGFAGQRFIDSTLEKIVELRKLREEHGYKYVIE

MDGSSNRKSFKKIYEAGPDIYIIGRSGLFGLHEDI

EKAWEIMCKDFEEMTGEKVL;

A6PE;
UniProt ID P32719;
*Escherichia coli*
SEQ ID NO: 5

MKISPSLMCMDLLKFKEQIEFIDSHADYFHIDIMD

GHFVPNLTLSPFFVSQVKKLATKPLDCHLMVTRPQ

DYIAQLARAGADFITLHPETINGQAFRLIDEIRRH

DMKVGLILNPETPVEAMKYYIHKADKITVMTVDPG

FAGQPFIPEMLDKLAELKAWREREGLEYEIEVDGS

CNQATYEKLMAAGADVFIVGTSGLFNHAENIDEAW

RIMTAQILAAKSEVQPHAKTA;

A6PE;
UniProt ID A8UV28;
*Hydrogenivirga* sp. 128-5-R1-1
SEQ ID NO: 6

MEKLLAPSILAGDWWNIGEQIEATLRGGADIIHFD

VMDGHFVPNITVGPEILTSISRRVNVPVDAHLMIE

NPDRYIPSFVEAGAKWISVHIENVPHIHRTLTLIR

ELGAKAGVVLNPGTPLSAVEEAIHYADYVLLMSVN

PGFSGQRFIERSLERLSLLRDMRDRLNPDCLIEVD

GGVKEDNVVEVVRAGADVVVVGSGIFSAKDVEAQT

RKLKDLISSAVAV;

A6PE;
UniParc ID UPI000411882A;
*Brevibacillus thermoruber*
SEQ ID NO: 7

MGFKFSPSLMCMNLLDIQHQIEVMNRRADLVHIDI

MDGHYVKNLTLSPFFIEQLKESLHVPMDVHLMVEN

PTDFIERVKEAGASIISPHAETINTDAFRIIDKVK

SLGCQMGIVLNPATPIAYIQHYIHLVDKITIMTVD

PGYAGQKFIPEMLEKIRQAKRLKEERGYRYLIEVD

GSCNVGTFKRLAEAGAEVFIVGSSGLFNLHPDLEV

AWDMMMDNFQREVGETTA;

A6PE; UniProt ID
G7M2I3;
*Clostridium* sp. DL-VIII
SEQ ID NO: 8

MKPMFAPSLMCANFLDLKNQIEILNERADIFHVDI

MDGHYVKNFSLSPAMMEQLKTITKIPMDAHLMVEN

PADFLEGIAKAGATYISPHAETINKDAFRIMRTIK

ALGCKTGVVLNPATPVEYIKHYLGMLDKITILTVD

AGFAGQTFIEEMLDKIEEVKRLREENGYSYLIEVD

GSCNEKTFKKLAEAGTEVFIVGSSGLFNLDADLKV

SWDKMMNMFNKCINN;

-continued

A6PE; UniProt ID A0A094WLM1; *Bacillus alcalophilus*

SEQ ID NO: 9

MYKFSPSLMCMDLSRFKEQVEVLNDKADFYHVDIM

DGHFVKNITLSPFFIQELKKITDVPIDAHLMVTNP

ADFVEMTIDAGADYISLHAETINGNAFRLINQIKE

KGKKFGVVLNPATPLESIRHYIQHVDKLTIMTVDP

GFAGQKFVEEMIGKIKEAKELKERNGYKYLITIDG

SCNKNTFKKLVEAGAEVLIVGSSGLFGLDEDVNIA

WDKMMDTFHLEVKDISQV;

A6PP; UniProt ID A3DC21; *Hungatelclostridium thermocellum*

SEQ ID NO: 10

MIKYKAVFFDFDYTLADSSKAVIECINYALQKMGY

PESSPESICRTIGLTLAEAFKILSGDTSDSNADLF

RQYFKERADLVMCDRTVMYSTVECVLKKLKKADVK

TGIVSTKYRYRIEDILKRDKLLQYFDVIVGGEDVA

AHKPDPEGLLKAISMVGCQKEEVLFVGDSTVDART

AKNAGVDFVAVLTGTTGANEFSEYNPGAVIEDLSG

LLDMFML;

A6PP; UniProt ID Q5LGR4; *Bacteroides fragilis*

SEQ ID NO: 11

MKYTVYLFDFDYTLADSSRGIVTCFRSVLERHGYT

GITDDMIKRTIGKTLEESFSILTGITDADQLESFR

QEYSKEADIYMNANTILFPDTLPTLTHLKKQGIRI

GIISTKYRFRILSFLRNHMPDDWFDIIIGGEDVTH

HKPDPEGLLLAIDRLKACPEEVLYIGDSTVDAGTA

AAAGVSFTGVTSGMTTAQEFQAYPYDRIISTLGQL

ISVPEDKSGCPL;

A6PP; UniProt ID Q89ZR1; *Bacteroides thetaiotaomicron*

SEQ ID NO: 12

MNYKTYLFDFDYTLADSSRGIVTCFRNVLNRHQYT

NVTDEAIKRTIGKTLEESFSILTGVTDWEQLTAFR

QEYRLEADVHMNVNTRLFPDTLSTLKELKERGARI

GIISTKYRFRILSFLDEYLPENFLDIVVGGEDVQA

AKPSPEGIKFALEHLGRTPQETLYIGDSTVDAETA

QNAGVDFAGVLNGMTTADELRAYPHRFIMENLSGL

LYI;

PGM; UniProt ID A0A150LLZ1; *Caldibacillus debilis*

SEQ ID NO: 13

MEWKQRAERWLRFENLDPELKKQLEEMAKDEKKLE

DLFYKYLEFGTGGMRGEIGPGTNRINIYTVRKASE

GLARFLLASGGEEKAKQGVVIAYDSRRKSREFALE

TAKTVGKHGIKAYVFESLRPTPELSFAVRYLHAAA

GVVITASHNPPEYNGYKVYGEDGGQLTPKAADELI

RYVYEVEDELSLTVPGEQELIDRGLLQYIGENIDL

AYIEKLKTIQLNRDVILNGGKDLKIVFTPLHGTAG

QLVQTGLREFGFQNVYVVKEQEQPDPDFSTVKSPN

PEEHEAFEIAIRYGKKYDADLIMGTDPDSDRLGIV

VKNGQGDYVVLTGNQTGAILLYYLLSQKKEKGMLV

RNSAVLKTIVTSELGRAIASDFGVETIDTLTGFKF

IGEKIKEFKETGSHVFQFGYEESYGYLIGDFVRDK

DAIQAALFAAEAAAYYKAQGKSLYDVLMEIYKKYG

FYKESLRSITLKGKDGAEKIRAIMDAFRQNPPEEV

SGIPVAITEDYLTQKRVDKAAGQTTPIHLPKSNVL

KYYLADESWFCIRPSGTEPKCKFYFAVRGDSEAQS

EARLRQLETNVMAMVEKILQK;

PGI; UniProt ID Q5SLL6; *Thermus thermophilus*

SEQ ID NO: 14

MLRLDTRFLPGFPEALSRHGPLLEEARRRLLAKRG

EPGSMLGWMDLPEDTETLREVRRYREANPWVEDFV

LIGIGGSALGPKALEAAFNESGVRFHYLDHVEPEP

ILRLLRTLDPRKTLVNAVSKSGSTAETLAGLAVFL

KWLKAHLGEDWRRHLVVTTDPKEGPLRAFAEREGL

KAFAIPKEVGGRFSALSPVGLLPLAFAGADLDALL

MGARKANETALAPLEESLPLKTALLLHLHRHLPVH

VFMVYSERLSHLPSWFVQLHDESLGKVDRQGQRVG

TTAVPALGPKDQHAQVQLFREGPLDKLLALVIPEA

PLEDVEIPEVEGLEAASYLFGKTLFQLLKAEAEAT

YEALAEAGQRVYALFLPEVSPYAVGWLMQHLMWQT

AFLGELWEVNAFDQPGVELGKVLTRKRLAG;

4GT; UniProt ID E8MXP8; *Anaerolinea thermophila*

SEQ ID NO: 15

MSLFKRASGILLHPTSLPGPDGIGDLGPEAYRWVN

FLAESGCSLWQILPLGPTGFGDSPYQCFSAFAGNP

YLVSPALLLDEGLLTSEDLADRPEFPASRVDYGPV

IQWKLTLLDRAYVRFKRSTSQKRKAAFEAFKEEQR

AWLLDFSLFMAIKEAHGGASWDYWPEPLRKRDPEA

LNAFHRAHEVDVERHSFRQFLFFRQWQALRQYAHE

KGVQIIGDVPIFVAYDSADVWSHPDLFYLDETGKP

TVVAGVPPDYFSATGQLWGNPLYRWDYHRETGFAW

WLERLKATFAMVDIVRLDHFRGFAGYWEVPYGMPT

AEKGRWVPGPGIALFEAIRNALGGLPIIAEDLGEI

TPDVIELREQLGLPGMKIFQFAFASDADDPFLPHN

YVQNCVAYTGTHDNDTAIGWYNSAPEKERDFVRRY

LARSGEDIAWDMIRAVWSSVAMFAIAPLQDFLKLG

PEARMNYPGRPAGNWGWRYEAFMLDDGLKNRIKEI

NYLYGRLPEHMKPPKVVKKWT;

αGP; UniProt ID G8NCC0;
*Thermus* sp. CCB_US3_UF1

SEQ ID NO: 16

MPLLPEPLSGLKELAYNLWWSWNPEAAELFQEIDP

SLWKRFRGNPVKLLLEADPGRLEGLAATSYPARVG

AVVEALRAYLREREEKQGPLVAYFSAEYGFHSSLP

IYSGGLGVLAGDHVKAASDLGLNLVGVGIFYHEGY

FHQRLSPEGVQVEVYETLHPEELPLYPVQDREGRP

LRVGVEFPGRTLWLSAYRVQVGAVPVYLLTANLPE

NTPEDRAITARLYAPGLEMRIQQELVLGLGGVRLL

RALGLAPEVFHMNEGHSAFLGLERVRELVAEGHPF

PVALELARAGALFTTHTPVPAGHDAFPLELVERYL

GGFWERMGTDRETFLSLGLEEKPWGKVFSMSNLAL

RTSAQANGVSRLHGEVSREMFHHLWPGFLREEVPI

GHVTNGVHTWTFLHPRLRRHYAEVFGPEWRKRPED

PETWKVEALGEEFWQIHKDLRAELVREVRTRLYEQ

RRRNGESPSRLREAEKVLDPEALTIGFARRFATYK

RAVLLFKDPERLRRLLHGHYPIQFVFAGKAHPKDE

PGKAYLQELFAKIREYGLEDRMVVLEDYDMYLARV

LVHGSDVWLNTPRRPMEASGTSGMKAALNGALNLS

VLDGWWAEAYNGKNGFAIGDERVYESEEAQDMADA

QALYDVLEFEVLPLFYAKGPEGYSSGWLSMVHESL

RTVGPRYSAARMVGDYLEIYRRGGAWAEAARAGQE

ALAAFHQALPALQGVTLRAQVPGDLTLNGVPMRVR

AFLEGEVPEALRPFLEVQLVVRRSSGHLEVVPMRP

GPDGYEVAYRPSRPGSYAYGVRLALRHPITGHVAW

VRWA;

What is claimed:

1. An improved process for the production of allulose from a saccharide, the improved process comprising the steps of:

converting fructose-6-phosphate (F6P) to allulose 6-phopsphate (A6P) using an allulose 6-phosphate epimerase (A6PE), wherein the A6PE comprises an amino acid sequence having at least 90% sequence identity to SEQ ID NO: 1; and converting A6P to allulose using an allulose 6-phosphate phosphatase (A6PP), wherein the improved process produces more allulose than a process for producing allulose under the same process conditions using *Bacillus thermoamylovorans* A6PE comprising the amino acid sequence as set forth in SEQ ID NO: 4.

2. An improved process for the production of allulose from a saccharide, the improved process comprising the steps of:

converting fructose-6-phosphate (F6P) to allulose 6-phopsphate (A6P) using an allulose 6-phosphate epimerase (A6PE); and converting A6P to allulose using an allulose-6-phoshpate phosphatase (A6PP), wherein the A6PP comprises the amino acid sequence as set forth in SEQ ID NO: 2, wherein the improved process produces more allulose than a process for producing allulose under the same process conditions using *Clostridium thermocellum* A6PP comprising the amino acid sequence as set forth in SEQ ID NO: 10.

3. The process of any one of claim 2, further comprising a step of converting glucose 6-phosphate (G6P) to the F6P, wherein the step is catalyzed by a phosphoglucoisomerase (PGI).

4. The process of claim 3, further comprising a step of converting glucose 1-phosphate (G1P) to the G6P, wherein the step is catalyzed by a phosphoglucomutase (PGM).

5. The process of claim 4, further comprising a step of converting a saccharide to the G1P, wherein the step is catalyzed by at least one enzyme, wherein the saccharide is selected from the group consisting of a starch or derivative thereof, cellulose or a derivative thereof and sucrose.

6. The process of claim 5, wherein the at least one enzyme is selected from the group consisting of alpha-glucan phosphorylase (αGP), maltose phosphorylase, sucrose phosphorylase, cellodextrin phosphorylase, cellobiose phosphorylase, and cellulose phosphorylase.

7. The process of claim 5, wherein the saccharide is starch or a derivative thereof selected from the group consisting of amylose, amylopectin, soluble starch, amylodextrin, maltodextrin, maltose, maltotriose, and glucose.

8. The process of claim 7, further comprising a step of converting starch to a starch derivative wherein the starch derivative is prepared by enzymatic hydrolysis of starch or by acid hydrolysis of starch.

9. The process of claim 8, wherein a 4-glucan transferase (4GT) is added to the process.

10. The process of claim 8, wherein the starch derivative is prepared by enzymatic hydrolysis of starch catalyzed by an isoamylase, a pullulanase, an alpha-amylase, or a combination thereof.

11. The process of claim 2, further comprising:

a step of converting fructose to F6P catalyzed by at least one enzyme; and optionally, a step of converting sucrose to fructose catalyzed by at least one enzyme.

12. The process of claim 3, further comprising:

a step of converting glucose to G6P catalyzed by at least one enzyme, and optionally, a step of converting sucrose to glucose catalyzed by at least one enzyme.

13. The process of claim 2, further comprising the steps of:

(i) converting a saccharide to glucose 1-phosphate (G1P) using an α-glucan phosphorylase or starch phosphorylase, wherein the saccharide is selected from the group consisting of starch, one or more derivatives of starch, or a combination thereof;

(ii) converting G1P to glucose 6-phosphate (G6P) using a phosphoglucomutase (PGM); and (iii) converting G6P to fructose 6-phosphate (F6P) using a phosphoglucoisomerase (PGI); wherein all process steps are conducted together in a single reaction vessel.

14. The process of claim 2, wherein the process steps are conducted under at least one of the following process conditions:

(a) at a temperature ranging from about 37° C. to about 85° C.;

(b) at a pH ranging from about 5.0 to about 9.0; or (c) for about 1 hour to about 48 hours.

15. The process of claim 13, wherein the process steps are conducted under at least one of the following process conditions:

(a) without adenosine triphosphate (ATP) as a source of phosphate;

(b) without nicotinamide adenosine dinucleotide;

(c) at a phosphate concentration from about 0.1 mM to about 150 mM;

(d) at a $Mg^{2+}$ concentration from about 0.1 mM to 50 mM;

(e) at a $Co^{2+}$ concentration from about 0.1 mM to 50 mM; and (f) wherein phosphate is recycled.

16. The process of claim 15, wherein phosphate is recycled, and wherein phosphate ions produced by A6PP dephosphorylation of A6P are used in the process step of converting a saccharide to G1P.

17. The process of any one of claim 13, further comprising the step of separating recovering the allulose produced, wherein the separation recovery is not via chromatography separation.

18. The process of claim 2 further comprising a step of adding the allulose to a consumable product.

19. The improved process of claim 1, wherein the A6PP comprises an amino acid sequence having at least 90% sequence identity to SEQ ID NO: 2.

* * * * *

SEQUENCE LISTING

```
<160> NUMBER OF SEQ ID NOS: 18

<210> SEQ ID NO 1
<211> LENGTH: 225
<212> TYPE: PRT
<213> ORGANISM: Thermoanaerobacterium thermosaccharolyticum

<400> SEQUENCE: 1

Met Lys Pro Met Phe Ala Pro Ser Leu Met Cys Ala Asn Phe Leu Asp
1               5                   10                  15

Leu Lys Asn Gln Ile Glu Ile Leu Asn Glu Arg Ala Asp Ile Tyr His
            20                  25                  30

Ile Asp Ile Met Asp Gly His Tyr Val Lys Asn Phe Ala Leu Ser Pro
        35                  40                  45

Tyr Leu Met Glu Gln Leu Lys Thr Ile Ala Lys Ile Pro Met Asp Ala
    50                  55                  60

His Leu Met Val Glu Asn Pro Ala Asp Phe Leu Glu Cys Ile Ala Lys
65                  70                  75                  80

Ser Gly Ala Thr Tyr Ile Ser Pro His Ala Glu Thr Ile Asn Lys Asp
                85                  90                  95

Ala Phe Arg Ile Met Arg Thr Ile Lys Ala Leu Gly Cys Lys Thr Gly
            100                 105                 110

Ile Val Leu Asn Pro Ala Thr Pro Val Glu Tyr Ile Lys Tyr Tyr Ile
        115                 120                 125

Gly Met Leu Asp Lys Ile Thr Ile Leu Thr Val Asp Ala Gly Phe Ala
    130                 135                 140

Gly Gln Thr Phe Ile Asn Glu Met Leu Asp Lys Ile Ala Glu Ile Lys
145                 150                 155                 160

Ser Leu Arg Asp Gln Asn Gly Tyr Ser Tyr Leu Ile Glu Val Asp Gly
                165                 170                 175

Ser Cys Asn Glu Lys Thr Phe Lys Gln Leu Ala Glu Ala Gly Thr Asp
            180                 185                 190

Val Phe Val Val Gly Ser Ser Gly Leu Phe Asn Leu Asp Thr Asp Leu
```

```
        195                 200                 205

Lys Val Ala Trp Asp Lys Met Met Asp Thr Phe Thr Arg Cys Thr Ser
    210                 215                 220

Asn
225


<210> SEQ ID NO 2
<211> LENGTH: 220
<212> TYPE: PRT
<213> ORGANISM: Methanosarcina thermophila

<400> SEQUENCE: 2

Met Leu Lys Ala Leu Ile Phe Asp Met Asp Gly Val Leu Val Asp Ser
1               5                   10                  15

Met Pro Phe His Ala Ala Ala Trp Lys Lys Ala Phe Phe Glu Met Gly
            20                  25                  30

Met Glu Ile Gln Asp Ser Asp Ile Phe Ala Ile Glu Gly Ser Asn Pro
        35                  40                  45

Arg Asn Gly Leu Pro Leu Leu Ile Arg Lys Ala Arg Lys Glu Pro Glu
    50                  55                  60

Ala Phe Asp Phe Glu Ala Ile Thr Ser Ile Tyr Arg Gln Glu Phe Lys
65                  70                  75                  80

Arg Val Phe Glu Pro Lys Ala Phe Glu Gly Met Lys Glu Cys Leu Glu
                85                  90                  95

Val Leu Lys Lys Arg Phe Leu Leu Ser Val Val Ser Gly Ser Asp His
            100                 105                 110

Val Ile Val His Ser Ile Ile Asn Arg Leu Phe Pro Gly Ile Phe Asp
        115                 120                 125

Ile Val Val Thr Gly Asp Asp Ile Ile Asn Ser Lys Pro His Pro Asp
    130                 135                 140

Pro Phe Leu Lys Ala Val Glu Leu Leu Asn Val Arg Arg Glu Glu Cys
145                 150                 155                 160

Val Val Ile Glu Asn Ala Ile Leu Gly Val Glu Ala Ala Lys Asn Ala
                165                 170                 175

Arg Ile Tyr Cys Ile Gly Val Pro Thr Tyr Val Glu Pro Ser His Leu
            180                 185                 190

Asp Lys Ala Asp Leu Val Val Glu Asp His Arg Gln Leu Met Gln His
        195                 200                 205

Leu Leu Ser Leu Glu Pro Ala Asn Gly Phe Arg Gln
    210                 215                 220


<210> SEQ ID NO 3
<211> LENGTH: 221
<212> TYPE: PRT
<213> ORGANISM: Thermoanaerobacterium thermosaccharolyticum

<400> SEQUENCE: 3

Met Lys Tyr Leu Phe Ser Pro Ser Leu Met Cys Met Asn Leu Ile Lys
1               5                   10                  15

Leu Asn Glu Gln Ile Ser Val Leu Asn Ser Lys Ala Asp Phe Leu His
            20                  25                  30

Val Asp Ile Met Asp Gly His Phe Val Lys Asn Ile Thr Leu Ser Pro
        35                  40                  45

Phe Phe Ile Glu Gln Ile Lys Ser Tyr Val Asn Ile Pro Ile Asp Ala
    50                  55                  60

His Leu Met Val Glu Asn Pro Gly Asp Tyr Ile Glu Ile Cys Glu Lys
```

```
65                  70                  75                  80

Ser Gly Ala Ser Phe Ile Thr Ile His Ala Glu Thr Ile Asn Arg Glu
                85                  90                  95

Ala Phe Arg Ile Ile Asp Arg Ile Lys Ser His Gly Leu Met Val Gly
            100                 105                 110

Ile Ala Leu Asn Pro Ala Thr Pro Ile Ser Glu Ile Lys His Tyr Ile
        115                 120                 125

Asn Lys Ile Asp Lys Ile Thr Ile Met Thr Val Asp Pro Gly Phe Ala
    130                 135                 140

Gly Gln Pro Phe Ile Pro Glu Val Leu Glu Lys Ile Arg Asp Leu Lys
145                 150                 155                 160

Arg Leu Lys Asp Asp Asn Asn Tyr Asn Tyr Leu Ile Glu Ala Asp Gly
                165                 170                 175

Ser Cys Asn Lys Asn Thr Phe Gln Val Leu Lys Asp Ala Gly Cys Lys
            180                 185                 190

Val Phe Val Leu Gly Ser Ser Gly Leu Phe Asn Leu Ser Asp Asp Leu
        195                 200                 205

Gly Lys Ala Trp Glu Ile Met Ile Gly Asn Phe Asn Gly
    210                 215                 220


<210> SEQ ID NO 4
<211> LENGTH: 230
<212> TYPE: PRT
<213> ORGANISM: Bacillus thermoamylovorans

<400> SEQUENCE: 4

Met Ser Asn Lys Ile Glu Phe Ser Pro Ser Leu Met Thr Met Asp Leu
1               5                   10                  15

Asp Lys Phe Lys Glu Gln Ile Thr Phe Leu Asn Asn His Val Gly Ser
            20                  25                  30

Tyr His Ile Asp Ile Met Asp Gly His Tyr Val Pro Asn Ile Thr Leu
        35                  40                  45

Ser Pro Trp Phe Val Gln Glu Val Arg Lys Ile Ser Asp Val Pro Met
    50                  55                  60

Ser Ala His Leu Met Val Thr Asn Pro Ser Phe Trp Val Gln Gln Leu
65                  70                  75                  80

Ile Asp Ile Lys Cys Glu Trp Ile Cys Met His Val Glu Thr Leu Asp
                85                  90                  95

Gly Leu Ala Phe Arg Leu Ile Asp Gln Ile His Asp Ala Gly Leu Lys
            100                 105                 110

Ala Gly Val Val Leu Asn Pro Glu Thr Ser Val Asp Ala Ile Arg Pro
        115                 120                 125

Tyr Ile Asp Leu Val Asp Lys Val Thr Ile Met Thr Val Asp Pro Gly
    130                 135                 140

Phe Ala Gly Gln Arg Phe Ile Asp Ser Thr Leu Glu Lys Ile Val Glu
145                 150                 155                 160

Leu Arg Lys Leu Arg Glu Glu His Gly Tyr Lys Tyr Val Ile Glu Met
                165                 170                 175

Asp Gly Ser Ser Asn Arg Lys Ser Phe Lys Lys Ile Tyr Glu Ala Gly
            180                 185                 190

Pro Asp Ile Tyr Ile Ile Gly Arg Ser Gly Leu Phe Gly Leu His Glu
        195                 200                 205

Asp Ile Glu Lys Ala Trp Glu Ile Met Cys Lys Asp Phe Glu Glu Met
    210                 215                 220
```

```
Thr Gly Glu Lys Val Leu
225                 230


<210> SEQ ID NO 5
<211> LENGTH: 231
<212> TYPE: PRT
<213> ORGANISM: Escherichia coli

<400> SEQUENCE: 5

Met Lys Ile Ser Pro Ser Leu Met Cys Met Asp Leu Leu Lys Phe Lys
1               5                   10                  15

Glu Gln Ile Glu Phe Ile Asp Ser His Ala Asp Tyr Phe His Ile Asp
            20                  25                  30

Ile Met Asp Gly His Phe Val Pro Asn Leu Thr Leu Ser Pro Phe Phe
        35                  40                  45

Val Ser Gln Val Lys Lys Leu Ala Thr Lys Pro Leu Asp Cys His Leu
    50                  55                  60

Met Val Thr Arg Pro Gln Asp Tyr Ile Ala Gln Leu Ala Arg Ala Gly
65                  70                  75                  80

Ala Asp Phe Ile Thr Leu His Pro Glu Thr Ile Asn Gly Gln Ala Phe
                85                  90                  95

Arg Leu Ile Asp Glu Ile Arg Arg His Asp Met Lys Val Gly Leu Ile
            100                 105                 110

Leu Asn Pro Glu Thr Pro Val Glu Ala Met Lys Tyr Tyr Ile His Lys
        115                 120                 125

Ala Asp Lys Ile Thr Val Met Thr Val Asp Pro Gly Phe Ala Gly Gln
    130                 135                 140

Pro Phe Ile Pro Glu Met Leu Asp Lys Leu Ala Glu Leu Lys Ala Trp
145                 150                 155                 160

Arg Glu Arg Glu Gly Leu Glu Tyr Glu Ile Glu Val Asp Gly Ser Cys
                165                 170                 175

Asn Gln Ala Thr Tyr Glu Lys Leu Met Ala Ala Gly Ala Asp Val Phe
            180                 185                 190

Ile Val Gly Thr Ser Gly Leu Phe Asn His Ala Glu Asn Ile Asp Glu
        195                 200                 205

Ala Trp Arg Ile Met Thr Ala Gln Ile Leu Ala Ala Lys Ser Glu Val
    210                 215                 220

Gln Pro His Ala Lys Thr Ala
225                 230


<210> SEQ ID NO 6
<211> LENGTH: 223
<212> TYPE: PRT
<213> ORGANISM: Hydrogenivirga sp. 128-5-R1-1

<400> SEQUENCE: 6

Met Glu Lys Leu Leu Ala Pro Ser Ile Leu Ala Gly Asp Trp Trp Asn
1               5                   10                  15

Ile Gly Glu Gln Ile Glu Ala Thr Leu Arg Gly Gly Ala Asp Ile Ile
            20                  25                  30

His Phe Asp Val Met Asp Gly His Phe Val Pro Asn Ile Thr Val Gly
        35                  40                  45

Pro Glu Ile Leu Thr Ser Ile Ser Arg Arg Val Asn Val Pro Val Asp
    50                  55                  60

Ala His Leu Met Ile Glu Asn Pro Asp Arg Tyr Ile Pro Ser Phe Val
65                  70                  75                  80
```

-continued

```
Glu Ala Gly Ala Lys Trp Ile Ser Val His Ile Glu Asn Val Pro His
                85                  90                  95

Ile His Arg Thr Leu Thr Leu Ile Arg Glu Leu Gly Ala Lys Ala Gly
            100                 105                 110

Val Val Leu Asn Pro Gly Thr Pro Leu Ser Ala Val Glu Glu Ala Ile
        115                 120                 125

His Tyr Ala Asp Tyr Val Leu Leu Met Ser Val Asn Pro Gly Phe Ser
    130                 135                 140

Gly Gln Arg Phe Ile Glu Arg Ser Leu Glu Arg Leu Ser Leu Leu Arg
145                 150                 155                 160

Asp Met Arg Asp Arg Leu Asn Pro Asp Cys Leu Ile Glu Val Asp Gly
                165                 170                 175

Gly Val Lys Glu Asp Asn Val Val Glu Val Val Arg Ala Gly Ala Asp
            180                 185                 190

Val Val Val Val Gly Ser Gly Ile Phe Ser Ala Lys Asp Val Glu Ala
        195                 200                 205

Gln Thr Arg Lys Leu Lys Asp Leu Ile Ser Ser Ala Val Ala Val
    210                 215                 220


<210> SEQ ID NO 7
<211> LENGTH: 228
<212> TYPE: PRT
<213> ORGANISM: Brevibacillus thermoruber

<400> SEQUENCE: 7

Met Gly Phe Lys Phe Ser Pro Ser Leu Met Cys Met Asn Leu Leu Asp
1               5                   10                  15

Ile Gln His Gln Ile Glu Val Met Asn Arg Arg Ala Asp Leu Val His
            20                  25                  30

Ile Asp Ile Met Asp Gly His Tyr Val Lys Asn Leu Thr Leu Ser Pro
        35                  40                  45

Phe Phe Ile Glu Gln Leu Lys Glu Ser Leu His Val Pro Met Asp Val
    50                  55                  60

His Leu Met Val Glu Asn Pro Thr Asp Phe Ile Glu Arg Val Lys Glu
65                  70                  75                  80

Ala Gly Ala Ser Ile Ile Ser Pro His Ala Glu Thr Ile Asn Thr Asp
                85                  90                  95

Ala Phe Arg Ile Ile Asp Lys Val Lys Ser Leu Gly Cys Gln Met Gly
            100                 105                 110

Ile Val Leu Asn Pro Ala Thr Pro Ile Ala Tyr Ile Gln His Tyr Ile
        115                 120                 125

His Leu Val Asp Lys Ile Thr Ile Met Thr Val Asp Pro Gly Tyr Ala
    130                 135                 140

Gly Gln Lys Phe Ile Pro Glu Met Leu Glu Lys Ile Arg Gln Ala Lys
145                 150                 155                 160

Arg Leu Lys Glu Glu Arg Gly Tyr Arg Tyr Leu Ile Glu Val Asp Gly
                165                 170                 175

Ser Cys Asn Val Gly Thr Phe Lys Arg Leu Ala Glu Ala Gly Ala Glu
            180                 185                 190

Val Phe Ile Val Gly Ser Ser Gly Leu Phe Asn Leu His Pro Asp Leu
        195                 200                 205

Glu Val Ala Trp Asp Met Met Met Asp Asn Phe Gln Arg Glu Val Gly
    210                 215                 220

Glu Thr Thr Ala
225
```

<210> SEQ ID NO 8
<211> LENGTH: 225
<212> TYPE: PRT
<213> ORGANISM: Clostridium sp. DL-VIII

<400> SEQUENCE: 8

```
Met Lys Pro Met Phe Ala Pro Ser Leu Met Cys Ala Asn Phe Leu Asp
1               5                   10                  15

Leu Lys Asn Gln Ile Glu Ile Leu Asn Glu Arg Ala Asp Ile Phe His
            20                  25                  30

Val Asp Ile Met Asp Gly His Tyr Val Lys Asn Phe Ser Leu Ser Pro
        35                  40                  45

Ala Met Met Glu Gln Leu Lys Thr Ile Thr Lys Ile Pro Met Asp Ala
    50                  55                  60

His Leu Met Val Glu Asn Pro Ala Asp Phe Leu Glu Gly Ile Ala Lys
65                  70                  75                  80

Ala Gly Ala Thr Tyr Ile Ser Pro His Ala Glu Thr Ile Asn Lys Asp
                85                  90                  95

Ala Phe Arg Ile Met Arg Thr Ile Lys Ala Leu Gly Cys Lys Thr Gly
            100                 105                 110

Val Val Leu Asn Pro Ala Thr Pro Val Glu Tyr Ile Lys His Tyr Leu
        115                 120                 125

Gly Met Leu Asp Lys Ile Thr Ile Leu Thr Val Asp Ala Gly Phe Ala
    130                 135                 140

Gly Gln Thr Phe Ile Glu Glu Met Leu Asp Lys Ile Glu Glu Val Lys
145                 150                 155                 160

Arg Leu Arg Glu Glu Asn Gly Tyr Ser Tyr Leu Ile Glu Val Asp Gly
                165                 170                 175

Ser Cys Asn Glu Lys Thr Phe Lys Lys Leu Ala Glu Ala Gly Thr Glu
            180                 185                 190

Val Phe Ile Val Gly Ser Ser Gly Leu Phe Asn Leu Asp Ala Asp Leu
        195                 200                 205

Lys Val Ser Trp Asp Lys Met Met Asn Met Phe Asn Lys Cys Ile Asn
    210                 215                 220

Asn
225
```

<210> SEQ ID NO 9
<211> LENGTH: 228
<212> TYPE: PRT
<213> ORGANISM: Bacillus alcalophilus

<400> SEQUENCE: 9

```
Met Tyr Lys Phe Ser Pro Ser Leu Met Cys Met Asp Leu Ser Arg Phe
1               5                   10                  15

Lys Glu Gln Val Glu Val Leu Asn Asp Lys Ala Asp Phe Tyr His Val
            20                  25                  30

Asp Ile Met Asp Gly His Phe Val Lys Asn Ile Thr Leu Ser Pro Phe
        35                  40                  45

Phe Ile Gln Glu Leu Lys Lys Ile Thr Asp Val Pro Ile Asp Ala His
    50                  55                  60

Leu Met Val Thr Asn Pro Ala Asp Phe Val Glu Met Thr Ile Asp Ala
65                  70                  75                  80

Gly Ala Asp Tyr Ile Ser Leu His Ala Glu Thr Ile Asn Gly Asn Ala
                85                  90                  95
```

```
Phe Arg Leu Ile Asn Gln Ile Lys Glu Lys Gly Lys Lys Phe Gly Val
            100                 105                 110

Val Leu Asn Pro Ala Thr Pro Leu Glu Ser Ile Arg His Tyr Ile Gln
        115                 120                 125

His Val Asp Lys Leu Thr Ile Met Thr Val Asp Pro Gly Phe Ala Gly
    130                 135                 140

Gln Lys Phe Val Glu Glu Met Ile Gly Lys Ile Lys Glu Ala Lys Glu
145                 150                 155                 160

Leu Lys Glu Arg Asn Gly Tyr Lys Tyr Leu Ile Thr Ile Asp Gly Ser
                165                 170                 175

Cys Asn Lys Asn Thr Phe Lys Lys Leu Val Glu Ala Gly Ala Glu Val
            180                 185                 190

Leu Ile Val Gly Ser Ser Gly Leu Phe Gly Leu Asp Glu Asp Val Asn
        195                 200                 205

Ile Ala Trp Asp Lys Met Met Asp Thr Phe His Leu Glu Val Lys Asp
    210                 215                 220

Ile Ser Gln Val
225


<210> SEQ ID NO 10
<211> LENGTH: 225
<212> TYPE: PRT
<213> ORGANISM: Thermoanaerobacterium thermosaccharolyticum

<400> SEQUENCE: 10

Met Lys Pro Met Phe Ala Pro Ser Leu Met Cys Ala Asn Phe Leu Asp
1               5                   10                  15

Leu Lys Asn Gln Ile Glu Ile Leu Asn Glu Arg Ala Asp Ile Tyr His
            20                  25                  30

Ile Asp Ile Met Asp Gly His Tyr Val Lys Asn Phe Ala Leu Ser Pro
        35                  40                  45

Tyr Leu Met Glu Gln Leu Lys Thr Ile Ala Lys Ile Pro Met Asp Ala
    50                  55                  60

His Leu Met Val Glu Asn Pro Ala Asp Phe Leu Glu Cys Ile Ala Lys
65                  70                  75                  80

Ser Gly Ala Thr Tyr Ile Ser Pro His Ala Glu Thr Ile Asn Lys Asp
                85                  90                  95

Ala Phe Arg Ile Met Arg Thr Ile Lys Ala Leu Gly Cys Lys Thr Gly
            100                 105                 110

Ile Val Leu Asn Pro Ala Thr Pro Val Glu Tyr Ile Lys Tyr Tyr Ile
        115                 120                 125

Gly Met Leu Asp Lys Ile Thr Ile Leu Thr Val Asp Ala Gly Phe Ala
    130                 135                 140

Gly Gln Thr Phe Ile Asn Glu Met Leu Asp Lys Ile Ala Glu Ile Lys
145                 150                 155                 160

Ser Leu Arg Asp Gln Asn Gly Tyr Ser Tyr Leu Ile Glu Val Asp Gly
                165                 170                 175

Ser Cys Asn Glu Lys Thr Phe Lys Gln Leu Ala Glu Ala Gly Thr Asp
            180                 185                 190

Val Phe Val Val Gly Ser Ser Gly Leu Phe Asn Leu Asp Thr Asp Leu
        195                 200                 205

Lys Val Ala Trp Asp Lys Met Met Asp Thr Phe Thr Arg Cys Thr Ser
    210                 215                 220

Asn
```

225

<210> SEQ ID NO 11
<211> LENGTH: 217
<212> TYPE: PRT
<213> ORGANISM: Hungateiclostridium thermocellum

<400> SEQUENCE: 11

```
Met Ile Lys Tyr Lys Ala Val Phe Phe Asp Phe Asp Tyr Thr Leu Ala
1               5                   10                  15

Asp Ser Ser Lys Ala Val Ile Glu Cys Ile Asn Tyr Ala Leu Gln Lys
            20                  25                  30

Met Gly Tyr Pro Glu Ser Ser Pro Glu Ser Ile Cys Arg Thr Ile Gly
        35                  40                  45

Leu Thr Leu Ala Glu Ala Phe Lys Ile Leu Ser Gly Asp Thr Ser Asp
    50                  55                  60

Ser Asn Ala Asp Leu Phe Arg Gln Tyr Phe Lys Glu Arg Ala Asp Leu
65                  70                  75                  80

Val Met Cys Asp Arg Thr Val Met Tyr Ser Thr Val Glu Cys Val Leu
                85                  90                  95

Lys Lys Leu Lys Lys Ala Asp Val Lys Thr Gly Ile Val Ser Thr Lys
            100                 105                 110

Tyr Arg Tyr Arg Ile Glu Asp Ile Leu Lys Arg Asp Lys Leu Leu Gln
        115                 120                 125

Tyr Phe Asp Val Ile Val Gly Gly Glu Asp Val Ala Ala His Lys Pro
    130                 135                 140

Asp Pro Glu Gly Leu Leu Lys Ala Ile Ser Met Val Gly Cys Gln Lys
145                 150                 155                 160

Glu Glu Val Leu Phe Val Gly Asp Ser Thr Val Asp Ala Arg Thr Ala
                165                 170                 175

Lys Asn Ala Gly Val Asp Phe Val Ala Val Leu Thr Gly Thr Thr Gly
            180                 185                 190

Ala Asn Glu Phe Ser Glu Tyr Asn Pro Gly Ala Val Ile Glu Asp Leu
        195                 200                 205

Ser Gly Leu Leu Asp Met Phe Met Leu
    210                 215
```

<210> SEQ ID NO 12
<211> LENGTH: 222
<212> TYPE: PRT
<213> ORGANISM: Bacteroides fragilis

<400> SEQUENCE: 12

```
Met Lys Tyr Thr Val Tyr Leu Phe Asp Phe Asp Tyr Thr Leu Ala Asp
1               5                   10                  15

Ser Ser Arg Gly Ile Val Thr Cys Phe Arg Ser Val Leu Glu Arg His
            20                  25                  30

Gly Tyr Thr Gly Ile Thr Asp Asp Met Ile Lys Arg Thr Ile Gly Lys
        35                  40                  45

Thr Leu Glu Glu Ser Phe Ser Ile Leu Thr Gly Ile Thr Asp Ala Asp
    50                  55                  60

Gln Leu Glu Ser Phe Arg Gln Glu Tyr Ser Lys Glu Ala Asp Ile Tyr
65                  70                  75                  80

Met Asn Ala Asn Thr Ile Leu Phe Pro Asp Thr Leu Pro Thr Leu Thr
                85                  90                  95

His Leu Lys Lys Gln Gly Ile Arg Ile Gly Ile Ile Ser Thr Lys Tyr
```

```
            100                 105                 110

Arg Phe Arg Ile Leu Ser Phe Leu Arg Asn His Met Pro Asp Asp Trp
        115                 120                 125

Phe Asp Ile Ile Ile Gly Gly Glu Asp Val Thr His His Lys Pro Asp
    130                 135                 140

Pro Glu Gly Leu Leu Leu Ala Ile Asp Arg Leu Lys Ala Cys Pro Glu
145                 150                 155                 160

Glu Val Leu Tyr Ile Gly Asp Ser Thr Val Asp Ala Gly Thr Ala Ala
                165                 170                 175

Ala Ala Gly Val Ser Phe Thr Gly Val Thr Ser Gly Met Thr Thr Ala
            180                 185                 190

Gln Glu Phe Gln Ala Tyr Pro Tyr Asp Arg Ile Ile Ser Thr Leu Gly
        195                 200                 205

Gln Leu Ile Ser Val Pro Glu Asp Lys Ser Gly Cys Pro Leu
    210                 215                 220


<210> SEQ ID NO 13
<211> LENGTH: 213
<212> TYPE: PRT
<213> ORGANISM: Bacteroides thetaiotaomicron

<400> SEQUENCE: 13

Met Asn Tyr Lys Thr Tyr Leu Phe Asp Phe Asp Tyr Thr Leu Ala Asp
1               5                   10                  15

Ser Ser Arg Gly Ile Val Thr Cys Phe Arg Asn Val Leu Asn Arg His
            20                  25                  30

Gln Tyr Thr Asn Val Thr Asp Glu Ala Ile Lys Arg Thr Ile Gly Lys
        35                  40                  45

Thr Leu Glu Glu Ser Phe Ser Ile Leu Thr Gly Val Thr Asp Trp Glu
    50                  55                  60

Gln Leu Thr Ala Phe Arg Gln Glu Tyr Arg Leu Glu Ala Asp Val His
65                  70                  75                  80

Met Asn Val Asn Thr Arg Leu Phe Pro Asp Thr Leu Ser Thr Leu Lys
                85                  90                  95

Glu Leu Lys Glu Arg Gly Ala Arg Ile Gly Ile Ile Ser Thr Lys Tyr
            100                 105                 110

Arg Phe Arg Ile Leu Ser Phe Leu Asp Glu Tyr Leu Pro Glu Asn Phe
        115                 120                 125

Leu Asp Ile Val Val Gly Gly Glu Asp Val Gln Ala Ala Lys Pro Ser
    130                 135                 140

Pro Glu Gly Ile Lys Phe Ala Leu Glu His Leu Gly Arg Thr Pro Gln
145                 150                 155                 160

Glu Thr Leu Tyr Ile Gly Asp Ser Thr Val Asp Ala Glu Thr Ala Gln
                165                 170                 175

Asn Ala Gly Val Asp Phe Ala Gly Val Leu Asn Gly Met Thr Thr Ala
            180                 185                 190

Asp Glu Leu Arg Ala Tyr Pro His Arg Phe Ile Met Glu Asn Leu Ser
        195                 200                 205

Gly Leu Leu Tyr Ile
    210


<210> SEQ ID NO 14
<211> LENGTH: 220
<212> TYPE: PRT
<213> ORGANISM: Methanosarcina thermophila
```

<400> SEQUENCE: 14

```
Met Leu Lys Ala Leu Ile Phe Asp Met Asp Gly Val Leu Val Asp Ser
1               5                   10                  15

Met Pro Phe His Ala Ala Ala Trp Lys Lys Ala Phe Phe Glu Met Gly
            20                  25                  30

Met Glu Ile Gln Asp Ser Asp Ile Phe Ala Ile Glu Gly Ser Asn Pro
        35                  40                  45

Arg Asn Gly Leu Pro Leu Leu Ile Arg Lys Ala Arg Lys Glu Pro Glu
    50                  55                  60

Ala Phe Asp Phe Glu Ala Ile Thr Ser Ile Tyr Arg Gln Glu Phe Lys
65                  70                  75                  80

Arg Val Phe Glu Pro Lys Ala Phe Glu Gly Met Lys Glu Cys Leu Glu
                85                  90                  95

Val Leu Lys Lys Arg Phe Leu Leu Ser Val Val Ser Gly Ser Asp His
            100                 105                 110

Val Ile Val His Ser Ile Ile Asn Arg Leu Phe Pro Gly Ile Phe Asp
        115                 120                 125

Ile Val Val Thr Gly Asp Asp Ile Ile Asn Ser Lys Pro His Pro Asp
    130                 135                 140

Pro Phe Leu Lys Ala Val Glu Leu Leu Asn Val Arg Arg Glu Glu Cys
145                 150                 155                 160

Val Val Ile Glu Asn Ala Ile Leu Gly Val Glu Ala Ala Lys Asn Ala
                165                 170                 175

Arg Ile Tyr Cys Ile Gly Val Pro Thr Tyr Val Glu Pro Ser His Leu
            180                 185                 190

Asp Lys Ala Asp Leu Val Val Glu Asp His Arg Gln Leu Met Gln His
        195                 200                 205

Leu Leu Ser Leu Glu Pro Ala Asn Gly Phe Arg Gln
    210                 215                 220
```

<210> SEQ ID NO 15
<211> LENGTH: 581
<212> TYPE: PRT
<213> ORGANISM: Caldibacillus debilis

<400> SEQUENCE: 15

```
Met Glu Trp Lys Gln Arg Ala Glu Arg Trp Leu Arg Phe Glu Asn Leu
1               5                   10                  15

Asp Pro Glu Leu Lys Lys Gln Leu Glu Glu Met Ala Lys Asp Glu Lys
            20                  25                  30

Lys Leu Glu Asp Leu Phe Tyr Lys Tyr Leu Glu Phe Gly Thr Gly Gly
        35                  40                  45

Met Arg Gly Glu Ile Gly Pro Gly Thr Asn Arg Ile Asn Ile Tyr Thr
    50                  55                  60

Val Arg Lys Ala Ser Glu Gly Leu Ala Arg Phe Leu Leu Ala Ser Gly
65                  70                  75                  80

Gly Glu Glu Lys Ala Lys Gln Gly Val Val Ile Ala Tyr Asp Ser Arg
                85                  90                  95

Arg Lys Ser Arg Glu Phe Ala Leu Glu Thr Ala Lys Thr Val Gly Lys
            100                 105                 110

His Gly Ile Lys Ala Tyr Val Phe Glu Ser Leu Arg Pro Thr Pro Glu
        115                 120                 125

Leu Ser Phe Ala Val Arg Tyr Leu His Ala Ala Ala Gly Val Val Ile
    130                 135                 140
```

-continued

```
Thr Ala Ser His Asn Pro Pro Glu Tyr Asn Gly Tyr Lys Val Tyr Gly
145                 150                 155                 160

Glu Asp Gly Gly Gln Leu Thr Pro Lys Ala Ala Asp Glu Leu Ile Arg
                165                 170                 175

Tyr Val Tyr Glu Val Glu Asp Glu Leu Ser Leu Thr Val Pro Gly Glu
            180                 185                 190

Gln Glu Leu Ile Asp Arg Gly Leu Leu Gln Tyr Ile Gly Glu Asn Ile
        195                 200                 205

Asp Leu Ala Tyr Ile Glu Lys Leu Lys Thr Ile Gln Leu Asn Arg Asp
    210                 215                 220

Val Ile Leu Asn Gly Gly Lys Asp Leu Lys Ile Val Phe Thr Pro Leu
225                 230                 235                 240

His Gly Thr Ala Gly Gln Leu Val Gln Thr Gly Leu Arg Glu Phe Gly
                245                 250                 255

Phe Gln Asn Val Tyr Val Val Lys Glu Gln Glu Gln Pro Asp Pro Asp
            260                 265                 270

Phe Ser Thr Val Lys Ser Pro Asn Pro Glu Glu His Glu Ala Phe Glu
        275                 280                 285

Ile Ala Ile Arg Tyr Gly Lys Lys Tyr Asp Ala Asp Leu Ile Met Gly
    290                 295                 300

Thr Asp Pro Asp Ser Asp Arg Leu Gly Ile Val Val Lys Asn Gly Gln
305                 310                 315                 320

Gly Asp Tyr Val Val Leu Thr Gly Asn Gln Thr Gly Ala Ile Leu Leu
                325                 330                 335

Tyr Tyr Leu Leu Ser Gln Lys Lys Glu Lys Gly Met Leu Val Arg Asn
            340                 345                 350

Ser Ala Val Leu Lys Thr Ile Val Thr Ser Glu Leu Gly Arg Ala Ile
        355                 360                 365

Ala Ser Asp Phe Gly Val Glu Thr Ile Asp Thr Leu Thr Gly Phe Lys
    370                 375                 380

Phe Ile Gly Glu Lys Ile Lys Glu Phe Lys Glu Thr Gly Ser His Val
385                 390                 395                 400

Phe Gln Phe Gly Tyr Glu Glu Ser Tyr Gly Tyr Leu Ile Gly Asp Phe
                405                 410                 415

Val Arg Asp Lys Asp Ala Ile Gln Ala Ala Leu Phe Ala Ala Glu Ala
            420                 425                 430

Ala Ala Tyr Tyr Lys Ala Gln Gly Lys Ser Leu Tyr Asp Val Leu Met
        435                 440                 445

Glu Ile Tyr Lys Lys Tyr Gly Phe Tyr Lys Glu Ser Leu Arg Ser Ile
    450                 455                 460

Thr Leu Lys Gly Lys Asp Gly Ala Glu Lys Ile Arg Ala Ile Met Asp
465                 470                 475                 480

Ala Phe Arg Gln Asn Pro Pro Glu Glu Val Ser Gly Ile Pro Val Ala
                485                 490                 495

Ile Thr Glu Asp Tyr Leu Thr Gln Lys Arg Val Asp Lys Ala Ala Gly
            500                 505                 510

Gln Thr Thr Pro Ile His Leu Pro Lys Ser Asn Val Leu Lys Tyr Tyr
        515                 520                 525

Leu Ala Asp Glu Ser Trp Phe Cys Ile Arg Pro Ser Gly Thr Glu Pro
    530                 535                 540

Lys Cys Lys Phe Tyr Phe Ala Val Arg Gly Asp Ser Glu Ala Gln Ser
545                 550                 555                 560

Glu Ala Arg Leu Arg Gln Leu Glu Thr Asn Val Met Ala Met Val Glu
```

```
                565                 570                 575

Lys Ile Leu Gln Lys
            580


<210> SEQ ID NO 16
<211> LENGTH: 415
<212> TYPE: PRT
<213> ORGANISM: Thermus thermophilus

<400> SEQUENCE: 16

Met Leu Arg Leu Asp Thr Arg Phe Leu Pro Gly Phe Pro Glu Ala Leu
1               5                   10                  15

Ser Arg His Gly Pro Leu Leu Glu Glu Ala Arg Arg Arg Leu Leu Ala
            20                  25                  30

Lys Arg Gly Glu Pro Gly Ser Met Leu Gly Trp Met Asp Leu Pro Glu
        35                  40                  45

Asp Thr Glu Thr Leu Arg Glu Val Arg Arg Tyr Arg Glu Ala Asn Pro
    50                  55                  60

Trp Val Glu Asp Phe Val Leu Ile Gly Ile Gly Gly Ser Ala Leu Gly
65                  70                  75                  80

Pro Lys Ala Leu Glu Ala Ala Phe Asn Glu Ser Gly Val Arg Phe His
                85                  90                  95

Tyr Leu Asp His Val Glu Pro Glu Pro Ile Leu Arg Leu Leu Arg Thr
            100                 105                 110

Leu Asp Pro Arg Lys Thr Leu Val Asn Ala Val Ser Lys Ser Gly Ser
        115                 120                 125

Thr Ala Glu Thr Leu Ala Gly Leu Ala Val Phe Leu Lys Trp Leu Lys
    130                 135                 140

Ala His Leu Gly Glu Asp Trp Arg Arg His Leu Val Val Thr Thr Asp
145                 150                 155                 160

Pro Lys Glu Gly Pro Leu Arg Ala Phe Ala Glu Arg Glu Gly Leu Lys
                165                 170                 175

Ala Phe Ala Ile Pro Lys Glu Val Gly Gly Arg Phe Ser Ala Leu Ser
            180                 185                 190

Pro Val Gly Leu Leu Pro Leu Ala Phe Ala Gly Ala Asp Leu Asp Ala
        195                 200                 205

Leu Leu Met Gly Ala Arg Lys Ala Asn Glu Thr Ala Leu Ala Pro Leu
    210                 215                 220

Glu Glu Ser Leu Pro Leu Lys Thr Ala Leu Leu Leu His Leu His Arg
225                 230                 235                 240

His Leu Pro Val His Val Phe Met Val Tyr Ser Glu Arg Leu Ser His
                245                 250                 255

Leu Pro Ser Trp Phe Val Gln Leu His Asp Glu Ser Leu Gly Lys Val
            260                 265                 270

Asp Arg Gln Gly Gln Arg Val Gly Thr Thr Ala Val Pro Ala Leu Gly
        275                 280                 285

Pro Lys Asp Gln His Ala Gln Val Gln Leu Phe Arg Glu Gly Pro Leu
    290                 295                 300

Asp Lys Leu Leu Ala Leu Val Ile Pro Glu Ala Pro Leu Glu Asp Val
305                 310                 315                 320

Glu Ile Pro Glu Val Glu Gly Leu Glu Ala Ala Ser Tyr Leu Phe Gly
                325                 330                 335

Lys Thr Leu Phe Gln Leu Leu Lys Ala Glu Ala Glu Ala Thr Tyr Glu
            340                 345                 350
```

```
Ala Leu Ala Glu Ala Gly Gln Arg Val Tyr Ala Leu Phe Leu Pro Glu
        355                 360                 365

Val Ser Pro Tyr Ala Val Gly Trp Leu Met Gln His Leu Met Trp Gln
    370                 375                 380

Thr Ala Phe Leu Gly Glu Leu Trp Glu Val Asn Ala Phe Asp Gln Pro
385                 390                 395                 400

Gly Val Glu Leu Gly Lys Val Leu Thr Arg Lys Arg Leu Ala Gly
                405                 410                 415


<210> SEQ ID NO 17
<211> LENGTH: 511
<212> TYPE: PRT
<213> ORGANISM: Anaerolinea thermophila

<400> SEQUENCE: 17

Met Ser Leu Phe Lys Arg Ala Ser Gly Ile Leu Leu His Pro Thr Ser
1               5                   10                  15

Leu Pro Gly Pro Asp Gly Ile Gly Asp Leu Gly Pro Glu Ala Tyr Arg
            20                  25                  30

Trp Val Asn Phe Leu Ala Glu Ser Gly Cys Ser Leu Trp Gln Ile Leu
        35                  40                  45

Pro Leu Gly Pro Thr Gly Phe Gly Asp Ser Pro Tyr Gln Cys Phe Ser
    50                  55                  60

Ala Phe Ala Gly Asn Pro Tyr Leu Val Ser Pro Ala Leu Leu Leu Asp
65                  70                  75                  80

Glu Gly Leu Leu Thr Ser Glu Asp Leu Ala Asp Arg Pro Glu Phe Pro
                85                  90                  95

Ala Ser Arg Val Asp Tyr Gly Pro Val Ile Gln Trp Lys Leu Thr Leu
            100                 105                 110

Leu Asp Arg Ala Tyr Val Arg Phe Lys Arg Ser Thr Ser Gln Lys Arg
        115                 120                 125

Lys Ala Ala Phe Glu Ala Phe Lys Glu Glu Gln Arg Ala Trp Leu Leu
    130                 135                 140

Asp Phe Ser Leu Phe Met Ala Ile Lys Glu Ala His Gly Gly Ala Ser
145                 150                 155                 160

Trp Asp Tyr Trp Pro Glu Pro Leu Arg Lys Arg Asp Pro Glu Ala Leu
                165                 170                 175

Asn Ala Phe His Arg Ala His Glu Val Asp Val Glu Arg His Ser Phe
            180                 185                 190

Arg Gln Phe Leu Phe Phe Arg Gln Trp Gln Ala Leu Arg Gln Tyr Ala
        195                 200                 205

His Glu Lys Gly Val Gln Ile Ile Gly Asp Val Pro Ile Phe Val Ala
    210                 215                 220

Tyr Asp Ser Ala Asp Val Trp Ser His Pro Asp Leu Phe Tyr Leu Asp
225                 230                 235                 240

Glu Thr Gly Lys Pro Thr Val Val Ala Gly Val Pro Pro Asp Tyr Phe
                245                 250                 255

Ser Ala Thr Gly Gln Leu Trp Gly Asn Pro Leu Tyr Arg Trp Asp Tyr
            260                 265                 270

His Arg Glu Thr Gly Phe Ala Trp Trp Leu Glu Arg Leu Lys Ala Thr
        275                 280                 285

Phe Ala Met Val Asp Ile Val Arg Leu Asp His Phe Arg Gly Phe Ala
    290                 295                 300

Gly Tyr Trp Glu Val Pro Tyr Gly Met Pro Thr Ala Glu Lys Gly Arg
305                 310                 315                 320
```

```
Trp Val Pro Gly Pro Gly Ile Ala Leu Phe Glu Ala Ile Arg Asn Ala
            325                 330                 335

Leu Gly Gly Leu Pro Ile Ile Ala Glu Asp Leu Gly Glu Ile Thr Pro
            340                 345                 350

Asp Val Ile Glu Leu Arg Glu Gln Leu Gly Leu Pro Gly Met Lys Ile
        355                 360                 365

Phe Gln Phe Ala Phe Ala Ser Asp Ala Asp Asp Pro Phe Leu Pro His
    370                 375                 380

Asn Tyr Val Gln Asn Cys Val Ala Tyr Thr Gly Thr His Asp Asn Asp
385                 390                 395                 400

Thr Ala Ile Gly Trp Tyr Asn Ser Ala Pro Glu Lys Glu Arg Asp Phe
                405                 410                 415

Val Arg Arg Tyr Leu Ala Arg Ser Gly Glu Asp Ile Ala Trp Asp Met
            420                 425                 430

Ile Arg Ala Val Trp Ser Ser Val Ala Met Phe Ala Ile Ala Pro Leu
        435                 440                 445

Gln Asp Phe Leu Lys Leu Gly Pro Glu Ala Arg Met Asn Tyr Pro Gly
    450                 455                 460

Arg Pro Ala Gly Asn Trp Gly Trp Arg Tyr Glu Ala Phe Met Leu Asp
465                 470                 475                 480

Asp Gly Leu Lys Asn Arg Ile Lys Glu Ile Asn Tyr Leu Tyr Gly Arg
                485                 490                 495

Leu Pro Glu His Met Lys Pro Pro Lys Val Val Lys Lys Trp Thr
            500                 505                 510


<210> SEQ ID NO 18
<211> LENGTH: 809
<212> TYPE: PRT
<213> ORGANISM: Thermus sp. CCB_US3_UF1

<400> SEQUENCE: 18

Met Pro Leu Leu Pro Glu Pro Leu Ser Gly Leu Lys Glu Leu Ala Tyr
1               5                   10                  15

Asn Leu Trp Trp Ser Trp Asn Pro Glu Ala Ala Glu Leu Phe Gln Glu
            20                  25                  30

Ile Asp Pro Ser Leu Trp Lys Arg Phe Arg Gly Asn Pro Val Lys Leu
        35                  40                  45

Leu Leu Glu Ala Asp Pro Gly Arg Leu Glu Gly Leu Ala Ala Thr Ser
    50                  55                  60

Tyr Pro Ala Arg Val Gly Ala Val Val Glu Ala Leu Arg Ala Tyr Leu
65                  70                  75                  80

Arg Glu Arg Glu Glu Lys Gln Gly Pro Leu Val Ala Tyr Phe Ser Ala
                85                  90                  95

Glu Tyr Gly Phe His Ser Ser Leu Pro Ile Tyr Ser Gly Gly Leu Gly
            100                 105                 110

Val Leu Ala Gly Asp His Val Lys Ala Ala Ser Asp Leu Gly Leu Asn
        115                 120                 125

Leu Val Gly Val Gly Ile Phe Tyr His Glu Gly Tyr Phe His Gln Arg
    130                 135                 140

Leu Ser Pro Glu Gly Val Gln Val Glu Val Tyr Glu Thr Leu His Pro
145                 150                 155                 160

Glu Glu Leu Pro Leu Tyr Pro Val Gln Asp Arg Glu Gly Arg Pro Leu
                165                 170                 175

Arg Val Gly Val Glu Phe Pro Gly Arg Thr Leu Trp Leu Ser Ala Tyr
```

```
            180                 185                 190

Arg Val Gln Val Gly Ala Val Pro Val Tyr Leu Leu Thr Ala Asn Leu
        195                 200                 205

Pro Glu Asn Thr Pro Glu Asp Arg Ala Ile Thr Ala Arg Leu Tyr Ala
    210                 215                 220

Pro Gly Leu Glu Met Arg Ile Gln Gln Glu Leu Val Leu Gly Leu Gly
225                 230                 235                 240

Gly Val Arg Leu Leu Arg Ala Leu Gly Leu Ala Pro Glu Val Phe His
                245                 250                 255

Met Asn Glu Gly His Ser Ala Phe Leu Gly Leu Glu Arg Val Arg Glu
            260                 265                 270

Leu Val Ala Glu Gly His Pro Phe Pro Val Ala Leu Glu Leu Ala Arg
        275                 280                 285

Ala Gly Ala Leu Phe Thr Thr His Thr Pro Val Pro Ala Gly His Asp
    290                 295                 300

Ala Phe Pro Leu Glu Leu Val Glu Arg Tyr Leu Gly Gly Phe Trp Glu
305                 310                 315                 320

Arg Met Gly Thr Asp Arg Glu Thr Phe Leu Ser Leu Gly Leu Glu Glu
                325                 330                 335

Lys Pro Trp Gly Lys Val Phe Ser Met Ser Asn Leu Ala Leu Arg Thr
            340                 345                 350

Ser Ala Gln Ala Asn Gly Val Ser Arg Leu His Gly Glu Val Ser Arg
        355                 360                 365

Glu Met Phe His His Leu Trp Pro Gly Phe Leu Arg Glu Glu Val Pro
    370                 375                 380

Ile Gly His Val Thr Asn Gly Val His Thr Trp Thr Phe Leu His Pro
385                 390                 395                 400

Arg Leu Arg Arg His Tyr Ala Glu Val Phe Gly Pro Glu Trp Arg Lys
                405                 410                 415

Arg Pro Glu Asp Pro Glu Thr Trp Lys Val Glu Ala Leu Gly Glu Glu
            420                 425                 430

Phe Trp Gln Ile His Lys Asp Leu Arg Ala Glu Leu Val Arg Glu Val
        435                 440                 445

Arg Thr Arg Leu Tyr Glu Gln Arg Arg Arg Asn Gly Glu Ser Pro Ser
    450                 455                 460

Arg Leu Arg Glu Ala Glu Lys Val Leu Asp Pro Glu Ala Leu Thr Ile
465                 470                 475                 480

Gly Phe Ala Arg Arg Phe Ala Thr Tyr Lys Arg Ala Val Leu Leu Phe
                485                 490                 495

Lys Asp Pro Glu Arg Leu Arg Arg Leu Leu His Gly His Tyr Pro Ile
            500                 505                 510

Gln Phe Val Phe Ala Gly Lys Ala His Pro Lys Asp Glu Pro Gly Lys
        515                 520                 525

Ala Tyr Leu Gln Glu Leu Phe Ala Lys Ile Arg Glu Tyr Gly Leu Glu
    530                 535                 540

Asp Arg Met Val Val Leu Glu Asp Tyr Asp Met Tyr Leu Ala Arg Val
545                 550                 555                 560

Leu Val His Gly Ser Asp Val Trp Leu Asn Thr Pro Arg Arg Pro Met
                565                 570                 575

Glu Ala Ser Gly Thr Ser Gly Met Lys Ala Ala Leu Asn Gly Ala Leu
            580                 585                 590

Asn Leu Ser Val Leu Asp Gly Trp Trp Ala Glu Ala Tyr Asn Gly Lys
        595                 600                 605
```

-continued

```
Asn Gly Phe Ala Ile Gly Asp Glu Arg Val Tyr Glu Ser Glu Glu Ala
    610                 615                 620

Gln Asp Met Ala Asp Ala Gln Ala Leu Tyr Asp Val Leu Glu Phe Glu
625                 630                 635                 640

Val Leu Pro Leu Phe Tyr Ala Lys Gly Pro Glu Gly Tyr Ser Ser Gly
                645                 650                 655

Trp Leu Ser Met Val His Glu Ser Leu Arg Thr Val Gly Pro Arg Tyr
            660                 665                 670

Ser Ala Ala Arg Met Val Gly Asp Tyr Leu Glu Ile Tyr Arg Arg Gly
        675                 680                 685

Gly Ala Trp Ala Glu Ala Ala Arg Ala Gly Gln Glu Ala Leu Ala Ala
    690                 695                 700

Phe His Gln Ala Leu Pro Ala Leu Gln Gly Val Thr Leu Arg Ala Gln
705                 710                 715                 720

Val Pro Gly Asp Leu Thr Leu Asn Gly Val Pro Met Arg Val Arg Ala
                725                 730                 735

Phe Leu Glu Gly Glu Val Pro Glu Ala Leu Arg Pro Phe Leu Glu Val
            740                 745                 750

Gln Leu Val Val Arg Arg Ser Ser Gly His Leu Glu Val Val Pro Met
        755                 760                 765

Arg Pro Gly Pro Asp Gly Tyr Glu Val Ala Tyr Arg Pro Ser Arg Pro
    770                 775                 780

Gly Ser Tyr Ala Tyr Gly Val Arg Leu Ala Leu Arg His Pro Ile Thr
785                 790                 795                 800

Gly His Val Ala Trp Val Arg Trp Ala
                805
```